United States Patent
Roh et al.

(10) Patent No.: US 11,710,559 B2
(45) Date of Patent: Jul. 25, 2023

(54) ADAPTIVE PATIENT CONDITION SURGICAL WARNING SYSTEM

(71) Applicant: IX Innovation LLC, Seattle, WA (US)

(72) Inventors: Jeffrey Roh, Seattle, WA (US); Justin Esterberg, Mercer Island, WA (US); John Cronin, Jericho, VT (US); Seth Cronin, Essex Junction, VT (US); Michael D'Andrea, Burlington, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/408,419

(22) Filed: Aug. 21, 2021

(65) Prior Publication Data

US 2023/0057961 A1     Feb. 23, 2023

(51) Int. Cl.
*G16H 40/40*     (2018.01)
*G16H 10/60*     (2018.01)
*G16H 20/40*     (2018.01)
*G06N 20/00*     (2019.01)

(52) U.S. Cl.
CPC ............. *G16H 40/40* (2018.01); *G06N 20/00* (2019.01); *G16H 10/60* (2018.01); *G16H 20/40* (2018.01)

(58) Field of Classification Search
CPC ......... G16H 40/40; G16H 20/40; G16H 10/60
See application file for complete search history.

(56) References Cited

U.S. PATENT DOCUMENTS

| | | | |
|---|---|---|---|
| 9,788,799 B2* | 10/2017 | Wagner | A61B 90/50 |
| 10,231,077 B2* | 3/2019 | Raduchel | G06Q 10/063 |
| 10,265,854 B2* | 4/2019 | Chen | A61B 34/30 |
| 10,540,438 B2* | 1/2020 | Nagarajan | G06F 40/237 |
| 10,949,975 B2* | 3/2021 | Bogoni | G16H 30/40 |
| 2008/0146893 A1* | 6/2008 | Levendowski | A61B 5/0002 600/300 |
| 2013/0244892 A1* | 9/2013 | Adourian | G16H 50/20 435/7.1 |
| 2013/0246088 A1* | 9/2013 | Huster | G06Q 10/0635 705/2 |
| 2014/0340219 A1* | 11/2014 | Russell | G08B 25/009 340/539.12 |
| 2018/0315507 A1* | 11/2018 | Mortazavi | G16H 50/30 |
| 2020/0170710 A1* | 6/2020 | Rus | G16H 20/40 |

(Continued)

*Primary Examiner* — Shahid Merchant
*Assistant Examiner* — Steven G. S. Sanghera
(74) *Attorney, Agent, or Firm* — Perkins Coie LLP

(57) ABSTRACT

Monitoring devices monitor physiological parameters of a patient undergoing surgery. The physiological parameters describe a physiological condition of the patient. A processor matches the physiological parameters to stored surgical data associated with adverse surgical events associated with surgical procedures matching the surgery. The processor determines a predicted time at which the physiological condition of the patient will meet a threshold physiological condition associated with the adverse surgical event based on a rate of change of the physiological parameters. Responsive to determining the predicted time, the processor transmits a first alert to robotic surgical controls to adjust the surgery prior to the predicted time. The processor determines that the physiological condition of the patient has met the threshold physiological condition. The processor transmits a second alert to the robotic surgical controls to terminate the surgery.

20 Claims, 9 Drawing Sheets

(56) References Cited

U.S. PATENT DOCUMENTS

2021/0076966 A1* 3/2021 Grantcharov ....... G06F 16/7867
2021/0313052 A1* 10/2021 Makrinich ............. A61B 90/94
2022/0241474 A1* 8/2022 Shelton, IV ......... A61B 5/0205

* cited by examiner

| Measure | Current | History | Standards | Rate of Change | Time to Threshold | Number of Similar Procedures | Number of Adverse Events |
|---|---|---|---|---|---|---|---|
| Blood pressure SBP | 92 mm Hg | SBP.dat | 90-130 mm Hg | -0.2/min | 20 minutes | 162 | 2 |
| Blood pressure DBP | 62 mm Hg | DBP.dat | 50-80 mm Hg | +0.1/min | 180 minutes | 225 | 3 |
| Blood oxygen percentage | 98 | O2.dat | 90% | -0.0/min | NA | 500 | 2 |
| Body Temperature | 36.2 | Temp.dat | 36C – 38C | -0.05/min | 4 minutes | 25 | 3 |

```
┌─────────────────────────────────────────────────────────────┐
│ Monitor, by one or more monitoring devices of a surgical    │
│ system, one or more physiological parameters of a patient   │
│ undergoing surgery, the one or more physiological           │
│ parameters describing a physiological condition of the      │
│ patient                                                     │
│ 804                                                         │
└─────────────────────────────────────────────────────────────┘
                              ↓
┌─────────────────────────────────────────────────────────────┐
│ Correlate, by one or more processors of the surgical        │
│ system, the one or more physiological parameters to stored  │
│ surgical data associated with one or more adverse surgical  │
│ events, the one or more adverse surgical events associated  │
│ with surgical procedures matching the surgery               │
│ 808                                                         │
└─────────────────────────────────────────────────────────────┘
                              ↓
┌─────────────────────────────────────────────────────────────┐
│ Determine, by the one or more processors of the surgical    │
│ system, a predicted time at which the physiological         │
│ condition of the patient will meet a threshold physiological│
│ condition associated with the adverse surgical event based  │
│ on a rate of change of the one or more physiological        │
│ parameters                                                  │
│ 812                                                         │
└─────────────────────────────────────────────────────────────┘
                              ↓
┌─────────────────────────────────────────────────────────────┐
│ Responsive to determining the predicted time, transmit, by  │
│ the one or more processors of the surgical system, a first  │
│ alert to one or more robotic surgical controls of the       │
│ surgical system to adjust the surgery prior to the predicted│
│ time                                                        │
│ 816                                                         │
└─────────────────────────────────────────────────────────────┘
                              ↓
┌─────────────────────────────────────────────────────────────┐
│ Determine, by the one or more processors of the surgical    │
│ system, that the physiological condition of the patient has │
│ met the threshold physiological condition                   │
│ 820                                                         │
└─────────────────────────────────────────────────────────────┘
                              ↓
┌─────────────────────────────────────────────────────────────┐
│ Responsive to determining that the physiological condition  │
│ of the patient has met the threshold physiological          │
│ condition, transmit, by the one or more processors of the   │
│ surgical system, a second alert to the one or more robotic  │
│ surgical controls to terminate the surgery                  │
│ 824                                                         │
└─────────────────────────────────────────────────────────────┘
```

*FIG. 8*

ADAPTIVE PATIENT CONDITION SURGICAL WARNING SYSTEM

TECHNICAL FIELD

The present disclosure is generally related to patient monitoring during surgical procedures and specifically to systems and methods for providing adaptive patient condition surgical warnings.

BACKGROUND

The risk of complications during surgery can include anesthesia complications, hemorrhaging, high blood pressure, a rise or fall in body temperature, etc. Such adverse events can occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on structured communication between the patient, the surgeon(s), and other members of the healthcare team. However, conventional methods are typically insufficient to prevent surgical errors and adverse events during surgery.

BRIEF DESCRIPTION OF THE DRAWINGS

FIG. 2 illustrates an example threshold database, in accordance with one or more embodiments.

FIG. 8 is a flow diagram illustrating an example process for an adaptive patient condition surgical warning system, in accordance with one or more embodiments.

DETAILED DESCRIPTION

Figure 1:
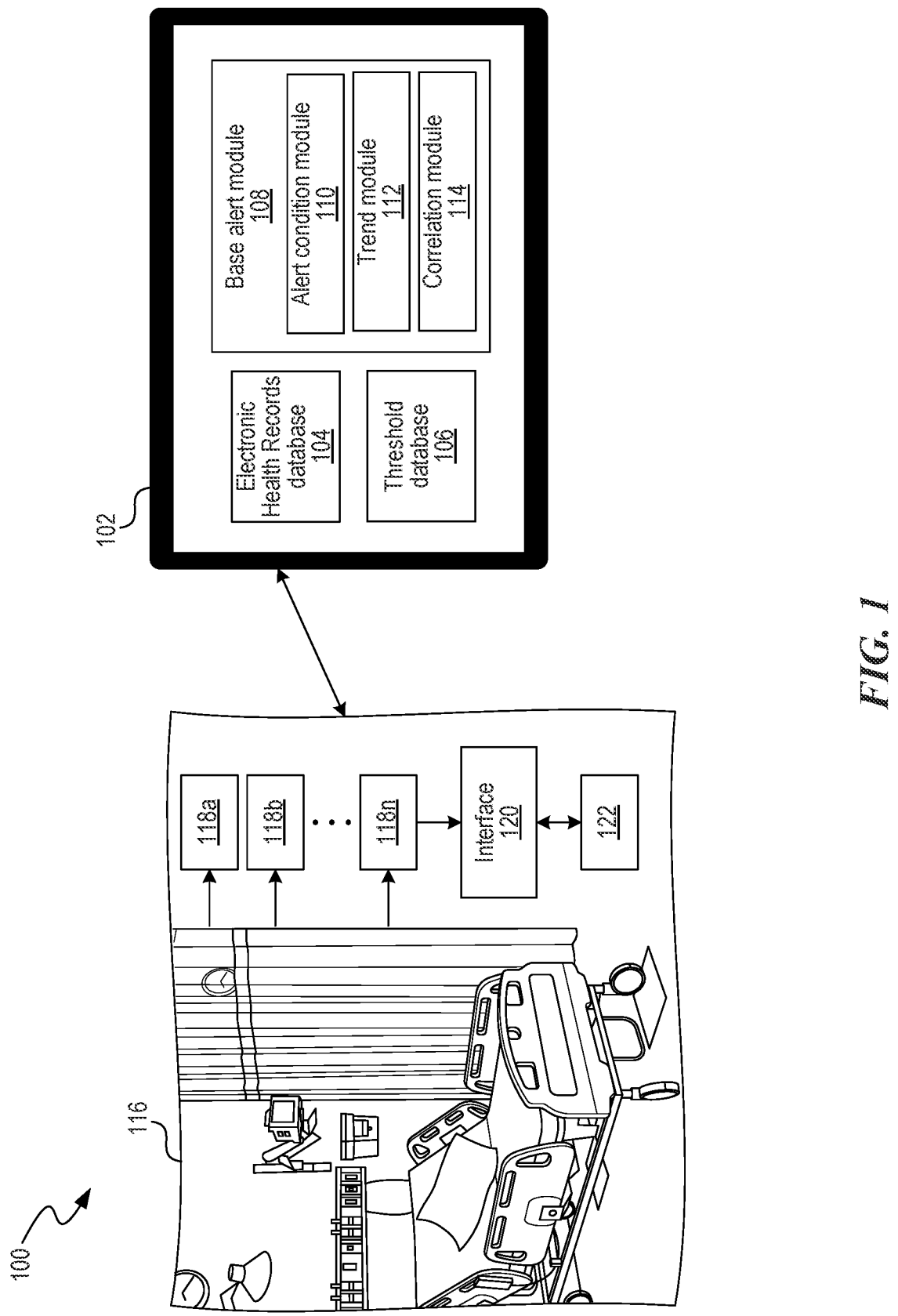
FIG. 1 is a block diagram illustrating an example adaptive patient condition surgical warning system, in accordance with one or more embodiments.

Embodiments of the present disclosure will be described more thoroughly from now on with reference to the accompanying drawings. Like numerals represent like elements throughout the several Figures, and in which example embodiments are shown. However, embodiments of the claims may be embodied in many different forms and should not be construed as limited to the embodiments set forth herein. The examples set forth herein are non-limiting examples and are merely examples, among other possible examples.

This document presents systems and apparatus for an adaptive patient condition surgical warning system. The embodiments disclosed herein describe an advanced surgical system that can include many different types of equipment to monitor and anesthetize the patient, assist the surgeon in performing surgical tasks, and maintain the environment of the operating room.

The advantages and benefits of the adaptive patient condition surgical warning system using at least some of the embodiments described herein include being compatible with best practice guidelines for alarm management in an operating room, e.g., from regulatory bodies and professional standards organizations such as the Association of Surgical Technologists. The methods disclosed avoid false alarms resulting in desensitization and neglect. The adaptive patient condition surgical warning system considers multiple variables, as well as trends and patterns in each of those variables, to deliver more accurate alerts to surgical staff to mitigate adverse events while reducing false alarms. The robotic technologies disclosed offer valuable enhancements to medical or surgical processes through improved precision, stability, and dexterity. The disclosed methods relieve medical personnel from routine tasks and make medical procedures safer and less costly for patients. The embodiments can also perform accurate surgery in smaller places and address the use of dangerous substances. Moreover, the adoption of robotic systems, according to at least some the embodiments disclosed herein, provides several benefits, including efficiency and speed improvements, lower costs, and higher accuracy.

In some embodiments, a system dynamically adapts alert criteria for a surgical monitoring system. The system can use trends in real-time sensor data to determine alert settings that can be different from standard "do not exceed" alert thresholds. The alert settings can be determined using historical data (e.g., from similar surgical procedures) to, for example, identify sensor data patterns that indicate a potentially adverse event. Patient-specific alert criteria can be determined based on the comparisons of real-time surgical monitoring sensor data and the historical reference data. The patient-specific alert criteria can be adjusted one or more times (e.g., periodically or continuously) during a surgical procedure based on, for example, the surgical step being performed, a present state of the patient, user input (e.g., physician input, surgical team input), etc.

In some embodiments, a method of dynamically adapting a surgical alert system includes receiving one or more physiological parameters of a patient measured by a monitoring system. The surgical alert system correlates the one or more physiological parameters to stored surgical data to determine one or more alert thresholds for the monitoring system. The physiological parameters can be analyzed to adjust the alert thresholds. In some embodiments, the alert thresholds are modified based on a surgical plan or step (e.g., a surgical step to be performed or being performed), expected acceptable changes in the patient's state, a patient's underlying health factors, or the like.

In some embodiments, apparatuses and systems for providing adaptive patient condition surgical warnings are disclosed. In some embodiments, one or more monitoring devices of a surgical system monitor one or more physiological parameters of a patient undergoing surgery. The one or more physiological parameters describe a physiological condition of the patient. One or more processors of the surgical system correlate the one or more physiological parameters to store surgical data associated with one or more adverse surgical events. The one or more adverse surgical events are associated with surgical procedures matching the surgery. The one or more processors of the surgical system determine a predicted time at which the physiological condition of the patient will meet a threshold physiological condition associated with the adverse surgical event based on a rate of change of the one or more physiological parameters. Responsive to determining the predicted time, the one or more processors of the surgical system transmit a first alert to one or more robotic surgical controls of the surgical system to adjust the surgery prior to the predicted time. The one or more processors of the surgical system determine that the physiological condition of the patient has met the threshold physiological condition. Responsive to determining that the physiological condition of the patient has met the threshold physiological condition, the one or more processors of the surgical system transmit a second alert to the one or more robotic surgical controls to terminate the surgery.

FIG. 1 is a block diagram illustrating an example adaptive patient condition surgical warning system 100, in accordance with one or more embodiments. The adaptive patient condition surgical warning system 100 includes a patient monitoring network or module 102 that monitors one or more sensors 118a-n. The patient monitoring network 102 is implemented using the components of the example computer system 900 illustrated and described in more detail with reference to FIG. 9. Likewise, embodiments of the system 100 may include different and/or additional components, or be connected in different ways.

The patient monitoring network 102 monitors a surgical procedure in an operating room 116. The operating room 116 is a facility, e.g., within a hospital, where surgical operations are carried out in an aseptic environment. Proper surgical procedures require a sterile field. In some embodiments, the sterile field is maintained in the operating room 116 in a medical care facility such as a hospital, doctor's office, or outpatient surgery center.

In some embodiments, the operating room 116 includes an anesthesiology machine that is used to generate and mix medical gases, like oxygen or air, and anesthetic agents to induce and maintain anesthesia in patients. Anesthesiology machines deliver oxygen and anesthetic gas to the patient, as well as filter out expiratory carbon dioxide. Anesthesia machines may perform functions such as providing oxygen ($O_2$), accurately mixing anesthetic gases and vapors, enabling patient ventilation, and minimizing anesthesia-related risks to patients and staff. Anesthesia machines may consist of the following essential components: a source of $O_2$, $O_2$ flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetic gases). Anesthesia machines may be divided into three parts: the high pressure system, the intermediate pressure system, and the low pressure system. The process of anesthesia starts with oxygen flow from a pipeline or cylinder through the flowmeter; the $O_2$ flows through the vaporizer and picks up the anesthetic vapors; the $O_2$-anesthetic mix then flows through the breathing circuit and into the patient's lungs, usually by spontaneous ventilation or normal respiration.

In some embodiments, the operating room 116 includes a surgical bed equipped with mechanisms that can elevate or lower the entire bed platform, flex, or extend individual components of the platform, or raise or lower the head or the feet of the patient independently. A surgical bed may be an operation bed, cardiac bed, amputation bed, or fracture bed. Some essential components of a surgical bed may be a bed sheet, woolen blanket, bath towel, and bed block. Surgical beds can also be referred to as postoperative beds, which refer to a special type of bed made for the patient who is coming from the operation theatre or from another procedure that requires anesthesia. The surgical bed is designed in a manner that makes it easier to transfer an unconscious or weak patient from a stretcher/wheelchair to the bed. The surgical bed should protect bed linen from vomiting, bleeding, drainage, and discharge; provide warmth and comfort to the patient to prevent shock; provide necessary position, which is suitable for operation; protect patient from being chilled; and be prepared to meet any emergency. Surgical beds can be integrated into the embodiments in a variety of manners.

In some embodiments, the operating room 116 includes a disposable air warmer (also referred to as Bair Hugger™), which refers to a convective temperature management system used in a hospital or surgery center to maintain a patient's core body temperature. The instrument consists of a reusable warming unit and a single-use disposable warming blanket for use during surgery, and it may also be used before and after surgery. The air warmer uses convective warming consisting of two components: a warming unit and a disposable blanket. The air warmer filters air and then forces warm air through disposable blankets which cover the patient. The blanket may be designed to use pressure points on the patient's body to prevent heat from reaching areas at risk for pressure sores or burns. The blanket may also include drain holes where fluid passes through the surface of the blanket to linen underneath, which will reduce the risk of skin softening and reduce the risk of unintended cooling because of heat loss from evaporation.

In some embodiments, the operating room 116 includes a sequential compression device (SCD) used to help prevent blood clots in the deep veins of legs. The SCD uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using an SCD may be discomfort, warmth, sweating beneath the cuff, skin breakdown, nerve damage, or pressure injury.

In some embodiments, the operating room 116 includes a Jackson frame (or Jackson table), which refers to a frame or table which is designed for use in spine surgeries and may be used in a variety of spinal procedures in supine, prone, or lateral positions in a safe manner. Two peculiar features of the Jackson table are no central table support and its ability to rotate the table through 180°. The Jackson table is supported at both ends, which keeps the whole of the table free. This allows the visualization of trunk and major parts of extremities as well. The Jackson frame allows the patient to be slid from the cart onto the table in the supine position with appropriate padding placed. The patient is then strapped securely on the table.

In some embodiments, the operating room 116 includes a bed position controller, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient may be in the following positions in a bed: supine position, prone position, lateral position, Sims' position, Fowler's position, semi-Fowler's position, orthopedic or tripod position, or Trendelenburg position.

In some embodiments, the operating room 116 includes operating room environmental controls for control or maintenance of the environment in an operation theatre where procedures are performed to minimize the risk of airborne infection and to provide a conducive environment for everyone in the operation theatre (e.g., surgeon, anesthesiologist, nurses, and patient). Some factors which may contribute to poor quality in the environment of the operating room 116 are temperature, ventilation, and humidity, and those conditions can lead to profound effects on the health and work productivity of people in the operating room 116. As an example: surgeons prefer a cool, dry climate since they work in bright, hot lights; anesthesia personnel prefer a warmer, less breezy climate; patient condition demands a relatively warm, humid, and quiet environment. Operating room environmental controls may control the environment by taking care of the following factors: environmental humidity, infection control, or odor control. Humidity control may be done by controlling the temperature of anesthesia gases; infection can be controlled by the use of filters to purify the air.

In some embodiments, the operating room 116 includes a heating, ventilation, and air conditioning (HVAC) system for regulating the environment of indoor settings by moving air between indoor and outdoor areas, along with heating and cooling. HVAC may use a different combination of systems, machines, and technologies to improve comfort. HVAC may be necessary to maintain the environment of an operating room. HVAC for an operating room may be a traditional operating room (which may have a large diffuser array directly above the operating table) or a hybrid operating room (which may have monitors and imaging equipment that consume valuable ceiling space and complicate the design process). HVAC may consist of three main units, for example, a heating unit (e.g., furnace or boiler), a ventilation unit (natural or forced), and an air conditioning unit (which may remove existing heat). HVAC may be made of components such as air returns, filters, exhaust outlets, ducts, electrical elements, outdoor units, compressors, coils, and blowers. The HVAC system may use central heating and AC systems that use a single blower to circulate air via internal ducts.

In some embodiments, the operating room 116 includes an air purification system for removing contaminants from the air in a room to improve indoor air quality. Air purification may be important in the operating room 116 as surgical site infection may be a reason for high mortality and morbidity. The air purification system may deliver clean, filtered, contaminant-free air over the operating room table with diffuser, airflow, etc., to remove all infectious particles down and away from the patient. Air purification systems may be an air curtain, multi-diffuser array, single large diffuser (based on laminar diffuser flow), or high-efficiency particulate air filter. A high-efficiency particulate air filter (HEPA filter) protects from infection and contamination by a filter which is mounted at the terminal of the duct. A HEPA filter may be mounted on the ceiling and deliver clean, filtered air in a flow to the room that provides a sweeping effect that pushes contaminants out via the return grilles that are usually mounted on the lower wall.

In some embodiments, orthopedic tools (also referred to as orthopedic instruments) are used for treatment and prevention of deformities and injuries of the musculoskeletal system or skeleton, articulations, and locomotive system (i.e., set formed by skeleton, muscles attached to it, and the part of the nervous system which controls the muscles). A major percentage of orthopedic tools are made of plastic. Orthopedic tools may be divided into the following specialties: hand and wrist, foot and ankle, shoulder and elbow, arthroscopic, hip, and knee. Orthopedic tools may be fixation tools, relieving tools, corrective tools, or compression-distraction tools. Fixation tool refers to a tool designed to restrict movements partially or completely in a joint, e.g., hinged splints (for preserving a certain range of movement in a joint) or rigid splints. Relieving tool refers to a tool designed to relieve pressure on an ailing part by transferring support to healthy parts of an extremity, e.g., the Thomas splint and the Voskoboinikova apparatus. Corrective tool refers to a tool designed to gradually correct a deformity, e.g., corsets, splints, orthopedic footwear, insoles, and other devices to correct abnormal positions of the foot. Compression-distraction tool refers to a tool designed to correct acquired or congenital deformities of the extremities, e.g., curvature, shortening, and pseudarthrosis such as Gudushauri. Fixation tools may be internal fixation tools (e.g., screws, plates) or external fixation tools (radius, tibia fracture fixation). Orthopedic tools may be bone-holding forceps, drill bits, nail pins, hammer, staple, etc.

In some embodiments, the operating room 116 includes a drill for making holes in bones for insertion of implants like nails, plates, screws, and wires. The drill tool functions by drilling cylindrical tunnels into bone. Drills may be used in orthopedics for performing medical procedures. If the drill does not stop immediately when used, the use of the drill on bones may have some risks, such as harm caused to bone, muscle, nerves, and venous tissues, which are wrapped by surrounding tissue. Drills vary widely in speed, power, and size. Drills may be powered as electrical, pneumatic, or battery. Drills generally may work on speeds below 1,000 rpm in orthopedics. Temperature control of drills is an important aspect in the functioning of the drill and is dependent on parameters such as rotation speed, torque, orthotropic site, sharpness of the cutting edges, irrigation, and cooling systems. The drill may comprise a physical drill, power cord, electronically motorized bone drill, and/or rotating bone shearing incision work unit.

In some embodiments, the operating room 116 includes a scalpel for slicing, cutting, or osteotomy of bone during orthopedic procedures. The scalpel may be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward-moving metal tip. Scalpels may prevent injuries caused by a drill in a spinal surgery, such as complications such as nerve thermal injury, grasping soft tissue, tearing dura mater, and mechanical injury.

In some embodiments, stitches (also referred to as sutures), or a sterile, surgical thread, are used to repair cuts or lacerations and are used to close incisions or hold body tissues together after a surgery or an injury. Stitches may involve the use of a needle along with an attached thread. Stitches may be of type absorbable (the stitches automatically break down harmlessly in the body over time without intervention) and non-absorbable (the stitches do not automatically break down over time and must be manually removed if not left indefinitely). Stitches may be based on material monofilament, multifilament, and barb. Stitches may be classified based on size. Stitches may be based on material synthetic and natural. Stitches may be based on coating coated and un-coated.

In some embodiments, a stapler is used for fragment fixation when inter-fragmental screw fixation is not easy. When there is vast damage and a bone is broken into fragments, staples can be used between these fragments for internal fixation and bone reconstruction. For example, they may be used around joints in ankle and foot surgeries, in cases of soft tissue damage, or to attach tendons or ligaments to the bone for reconstruction surgery. Staplers may be made of surgical grade stainless steel or titanium, and they are thicker, stronger, and larger.

In some embodiments, equipment, such as a set of articles, tools, or objects, is used to implement or achieve an operation or activity. Medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment may perform functions invasively or non-invasively. The medical equipment may consist of components such as sensor/transducer, signal conditioner, display, data storage unit, etc. The medical equipment works by taking a signal from a measurand/patient; a transducer for converting one form of energy to electrical energy; a signal conditioner such as an amplifier, filter, etc., to convert the output from the transducer into an electrical value; a display to provide a visual representation of the measured parameter or quantity; and a storage system to store data which can be used for future reference. The medical equipment may perform any function of diagnosis or provide therapy; for example, the equipment delivers air into the lungs of a patient who is physically unable to breathe, or breaths insufficiently, and moves it out of the lungs.

In some embodiments, the operating room 116 includes a ventilator (also referred to as a respirator), which provides a patient with oxygen when they are unable to breathe on their own. The ventilator is required when a person is not able to breathe on their own. The ventilator may perform a function of gently pushing air into the lungs (like lungs when they are working) and allows it to come back out. A ventilator functions by delivery of positive pressure to force air into the lungs, while usual breathing uses negative pressure by the opening of the mouth, and air flows in. A ventilator may be required during surgery or after surgery. A ventilator may be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator may be used with a face mask (non-invasive ventilation, where the ventilation is required for a shorter duration of time) or with a breathing tube, also referred to as an endotracheal tube (invasive ventilation, where the ventilation is required for a longer duration of time). Ventilator use may have some risks such as infections, fluid build-up, muscle weakness, lung damage, etc. A ventilator may be operated in various modes, such as assist-control ventilation (ACV), synchronized intermittent-mandatory ventilation (SIMV), pressure-controlled ventilation (PCV), pressure support ventilation (PSV), pressure controlled inverse ratio ventilation (PCIRV), airway pressure release ventilation (APRV), etc. A ventilator may comprise a gas delivery system, power source, control system, safety feature, gas filter, and monitor.

In some embodiments, a continuous positive airway pressure (CPAP) machine is used for the treatment of sleep apnea disorder in a patient. Sleep apnea refers to a disorder in which breathing repeatedly stops and starts while a patient is sleeping, often because the throat/airways briefly collapse or something temporarily blocks them. Sleep apnea may lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine may work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs the oxygen. This helps the patient to not wake up to resume breathing. The CPAP instrument may have a nasal pillow mask, nasal mask, or full mask. The CPAP instrument may comprise a motor, a cushioned mask, a tube that connects the motor to the mask, a headgear frame, and adjustable straps. The essential components may be a motor, a cushioned mask, and a tube that connects the motor to the mask.

In some embodiments, equipment tracking systems, such as radio-frequency identification (RFID), are used to tag an instrument with an electronic tag and track it using the tag. Typically, this could involve a centralized platform that provides details such as location, owner, contract, and maintenance history for all equipment in real-time. A variety of techniques can be used to track physical assets, including RFID, a global positioning system (GPS), Bluetooth low energy (BLE), barcodes, near-field communication (NFC), Wi-Fi, etc. The equipment tracking system comprises the hardware components, such as RFID tags, GPS trackers, barcodes, and QR codes. The hardware component is placed on the asset, and it communicates with the software (directly or via a scanner), providing the software with data about the asset's location and properties. An equipment tracking system uses electromagnetic fields to transmit data from an RFID tag to a reader. Reading of RFID tags may be done by portable or mounted RFID readers. RFID may be very short for low frequency or high frequency for ultra-high frequency. Managing and locating important assets is a key challenge for tracking medical equipment. Time spent searching for critical equipment can lead to expensive delays or downtime, missed deadlines and customer commitments, and wasted labor. The problem has been solved by using barcode labels or manual serial numbers and spreadsheets; however, these require manual labor. The RFID tag may be passive (smaller and less expensive, read ranges are shorter, have no power of their own, and are powered by the radio frequency energy transmitted from RFID readers/antennas) or active (larger and more expensive, read ranges are longer, have a built-in power source, and a transmitter of their own). Equipment tracking systems may offer advantages, such as no line of sight required, read multiple RFID objects at once, scan at a distance, and flexibility.

One or more monitoring devices or sensors 118a-n monitor one or more physiological parameters of a patient undergoing surgery. The one or more physiological parameters describe a physiological condition of the patient. In some embodiments, the one or more monitoring devices include at least one of a heart-rate monitor, pulse oximeter, capnography monitor, blood pressure monitor, body temperature monitor, or electrocardiogram machine. The operating room 116 contains the one or more sensors 118a-n. The sensors 118, such as microphones or optical sensors, can produce images or video captured from at least one of multiple imaging devices, for example, cameras attached to the manipulators or end-effectors, cameras mounted to the ceiling or other surface above the surgical theatre, or cameras mounted on a tripod or other independent mounting device. In some embodiments, the cameras are body worn by a surgeon or other surgical staff, the cameras are incorporated into a wearable device, such as an augmented reality device like Google Glass, or the cameras are integrated into an endoscopic, microscopic, or laparoscopic device. In some embodiments, a camera or other imaging device (e.g., ultrasound) present in the surgical theatre is associated with one or more areas in the operating room 116. The sensors 118 can be associated with measuring a specific parameter of the patient, such as respiratory rate, blood pressure, blood oxygen level, heart rate, etc.

In some embodiments, the one or more sensors 118a-n include a vital signs monitor 118a (a medical diagnostic instrument), which can be a portable, battery powered, multi-parametric, vital signs monitoring device used for both ambulatory and transport applications, as well as bedside monitoring. The vital signs monitor 118a can be used with an isolated data link to an interconnected portable computer allowing snapshot and trended data from the vital signs monitor 118a to be printed automatically at the patient monitoring network 102, and also allowing default configuration settings to be downloaded to the vital signs monitor 118a. The vital signs monitor 118a is capable of use as a stand-alone unit, as well as part of a bi-directional wireless communications network that includes at least one remote monitoring station (e.g., the patient monitoring network 102). The vital signs monitor 118a can measure multiple physiologic parameters of a patient wherein various sensor output signals are transmitted either wirelessly or by means of a wired connection to at least one remote site, such as the patient monitoring network 102.

In some embodiments, the one or more sensors 118a-n include a heart-rate monitor 118b, which is a sensor and/or a sensor system applied in the context of monitoring heart rates. The heart-rate monitor 118b measures, directly or indirectly, any physiological condition from which any relevant aspect of heart rate can be gleaned. For example, some embodiments of the heart-rate monitor 118b measure different or overlapping physiological conditions to measure the same aspect of heart rate. Alternatively, some embodiments measure the same, different, or overlapping physiological conditions to measure different aspects of heart rate, i.e., number of beats, strength of beats, regularity of beats, beat anomalies, etc.

In some embodiments, the one or more sensors 118a-n include a pulse oximeter 118n or $SpO_2$ monitor, which is a plethysmograph or any instrument that measures variations in the size of an organ or body part of the patient on the basis of the amount of blood passing through or present in the part. The pulse oximeter 118n is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter 118n can include a light sensor that is placed at a site on the patient, usually a fingertip, toe, forehead, or earlobe, or in the case of a neonate, across a foot. Light, which can be produced by a light source integrated into the pulse oximeter 118n, containing both red and infrared wavelengths, is directed onto the skin of the patient, and the light that passes through the skin is detected by the pulse oximeter 118n. The intensity of light in each wavelength is measured by the pulse oximeter 118n over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the one or more sensors 118a-n include an end-tidal $CO_2$ monitor or capnography monitor, used for measurement of the level of carbon dioxide (referred to as end-tidal carbon dioxide, $EtCO_2$) that is released at the end of an exhaled breath. An end-tidal $CO_2$ monitor or capnography monitor is widely used in anesthesia and intensive care. $EtCO_2$ can be calculated by plotting expiratory $CO_2$ with time. Further, $EtCO_2$ monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end-tidal $CO_2$ monitor can be configured as side stream (diverting) or mainstream (non-diverting). A diverting end-tidal $CO_2$ monitor transports a portion of a patient's respired gases from the sampling site to the end-tidal $CO_2$ monitor, while a non-diverting end-tidal $CO_2$ monitor does not transport gas away. Also, measurement by the end-tidal $CO_2$ monitor is based on the absorption of infrared light by carbon dioxide, where exhaled gas passes through a sampling chamber containing an infrared light source and photodetector on both sides. Based on the amount of infrared light reaching the photodetector, the amount of carbon dioxide present in the gas can be calculated.

In some embodiments, the one or more sensors 118a-n include a blood pressure monitor that measures blood pressure, particularly in arteries. The blood pressure monitor uses a non-invasive technique (by external cuff application) or an invasive technique (by a cannula needle inserted in the artery, used in the operating room 116) for measurement. The non-invasive method (referred to as a sphygmomanometer) works by measurement of force exerted against arterial walls during ventricular systole (i.e., systolic blood pressure occurs when the heart beats and pushes blood through the arteries) and ventricular diastole (i.e., diastolic blood pressure occurs when the heart rests and is filling with blood), thereby measuring systole and diastole, respectively. The blood pressure monitor can be of three types: automatic/digital, manual (aneroid-dial), and manual (mercury-column). The sphygmomanometer may include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the one or more sensors 118a-n include a body temperature monitor. The body temperature monitor measures the temperature invasively or non-invasively by placement of a sensor into organs such as bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the one or more sensors 118a-n measure respiration rate or breathing rate, which is the rate at which breathing occurs, and is measured by the number of breaths the patient takes per minute. The rate is measured when a person is at rest and simply involves counting the number of breaths for one minute by counting how many times the chest rises. Normal respiration rates for an adult patient at rest are in the range of 12 to 16 breaths per minute. A variation can be an indication of an abnormality/medical condition or the patient's demographic parameters. The sensors 118a-n can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can bring a change to the respiration rate, thereby increasing or reducing the respiration rate from normal levels.

In some embodiments, the one or more sensors 118a-n measure an electrocardiogram (EKG or ECG), a representation of the electrical activity of the heart (graphical trace of voltage versus time) by placement of electrodes on the skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia where the heart rate becomes faster and bradycardia where the heart rate becomes slower), coronary heart disease, heart attacks, or cardiomyopathy. The instrument used for measurement of the electrocardiogram is called an electrocardiograph, which measures the electrical impulses by the placement of electrodes on the surface of the body and represents the ECG by a PQRST waveform. PQRST wave is read as: P wave, which represents the depolarization of the left and right atrium and corresponding to atrial contraction; QRS complex, which indicates ventricular depolarization and represents the electrical impulse as it spreads through the ventricles; and T wave, which indicates ventricular repolarization and follows the QRS complex.

In some embodiments, the one or more sensors 118a-n perform neuromonitoring, also called intraoperative neurophysiological monitoring (IONM). The sensors 118a-n assess functions and changes in the brain, brainstem, spinal cord, cranial nerves, and peripheral nerves during a surgical procedure on these organs. Monitoring includes both continuous monitoring of neural tissue, as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and sensorimotor cortex, which helps in guiding the surgeon during dissection. Electrophysiological modalities employed in neuromonitoring are an extracellular single unit and local field potential (LFP) recordings, somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the one or more sensors 118a-n measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways, specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the one or more sensors 118a-n measure somatosensory evoked potential (SSEP or SEP), the electrical signals elicited by the brain and the spinal cord in response to sensory stimulus or touch. SSEP is used for intraoperative neurophysiological monitoring in spinal surgeries. The measurements are reliable, which allow for continuous monitoring during a surgical procedure. The sensor stimulus commonly given to the organs can be auditory, visual, or somatosensory SEPs and applied on the skin, peripheral nerves of the upper limb, lower limb, or scalp. The stimulation technique can be mechanical, electrical (provides larger and more robust responses), or intraoperative spinal monitoring modality.

In some embodiments, the one or more sensors 118a-n provide electromyography (EMG), the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation, and does not perform external stimulation. Spontaneous EMG is recorded by the insertion of a needle electrode. Triggered EMG refers to the recording of myoelectric signals during stimulation of target site, such as pedicle screws with incremental current intensities.

In some embodiments, the one or more sensors 118a-n provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the one or more sensors 118a-n include a medical visualization apparatus used for visualization and analysis of objects (preferably three-dimensional (3D) objects) in the operating room 116. The medical visualization apparatus provides the selection of points at surfaces, selection of a region of interest, or selection of objects. Medical visualization systems can also be used for diagnosis, treatment planning, intraoperative support, documentation, or educational purposes. Medical visualization systems can further include microscopes, endoscopes/arthroscopes/laparoscopes, fiber optics, surgical lights, high-definition monitors, operating room cameras, etc. Three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the one or more sensors 118a-n include a microscope used for viewing samples and objects that cannot be seen with an unaided eye. The microscope can have components such as eyepieces, objective lenses, adjustment knobs, a stage, an illuminator, a condenser, or a diaphragm. A microscope works by manipulating how light enters the eye using a convex lens, where both sides of the lens are curved outwards. When light reflects off of an object being viewed under the microscope and passes through the lens, it bends toward the eye. This makes the object look bigger than it is. A microscope can be compound (light illuminated and image seen with the microscope is two dimensional), dissection or stereoscope (light illuminated and image seen with the microscope is three dimensional), confocal (laser-illuminated and image seen with the microscope is on a digital computer screen), scanning electron (SEM) (electron illuminated and image seen with the microscope is in black and white), or transmission electron microscope (TEM) (electron illuminated and image seen with the microscope is the high magnification and high resolution).

In some embodiments, the patient monitoring network 102 is communicatively coupled to the sensors 118a-n in the operating room 116 by a direct connection, such as ethernet, or wirelessly by the cloud or local network. The patient monitoring network 102 can communicate with the sensors 118a-n using the network adapter 912 and network 914 illustrated and described in more detail with reference to FIG. 9. The patient monitoring network 102 can dynamically adjust alert criteria using real-time surgical monitoring sensor data to determine alert thresholds based on prior-patient data from similar surgical procedures. Patient-specific alert criteria can be determined based on comparisons of real-time surgical monitoring sensor data and historical reference data. The patient-specific alert criteria can be adjusted (e.g., periodically or continuously) during a surgical procedure based on, for example, a surgical plan, the surgical step being performed, a current state of the patient, user input (e.g., physician input, surgical team input), etc.

In some embodiments, a surgical system 122 dynamically adapts alert criteria for a patient surgical monitoring system. The surgical system 122 is implemented using components of the computer system 900 illustrated and described in more detail with reference to FIG. 9. The surgical system 122 can use trends in real-time sensor data to determine alert settings that are different from standard "do not exceed" alert thresholds. The alert settings can be determined using historical data (e.g., from similar surgical procedures) to, for example, identify sensor data patterns that indicate a potentially adverse event. Patient-specific alert criteria can be determined based on the comparisons of real-time surgical monitoring sensor data and the historical reference data. The patient-specific alert criteria can be adjusted one or times (e.g., periodically or continuously) during a surgical procedure based on, for example, a surgical step being performed, a current state of a patient, user input (e.g., physician input, surgical team input), etc.

The patient monitoring network 102 can determine a predicted time at which a physiological condition of the patient will meet a threshold physiological condition associated with an adverse surgical event based on a rate of change of one or more physiological parameters of the patient. In some embodiments, the patient monitoring network 102 or the surgical system 122 determines a schedule of predicted times for adverse surgical events and confidence scores. The schedule can be updated in real-time to monitor the effects of one or more adjustments to a surgical plan. The patient monitoring network 102 can display a monitoring plan with settings (e.g., settings for monitoring sensors), predicted adverse event times, alert thresholds, confidence scores, and/or collected data for viewing by the physician and/or surgical team. The patient monitoring network 102 can receive user input to modify the monitoring plan, surgical plan, etc. The patient monitoring network 102 can be a computing device, such as a computer, tablet, smartphone, smart speaker, etc. The patient monitoring network 102 is implemented using components of the example computer system 900 illustrated and described in more detail with reference to FIG. 9. The patient monitoring network 102 includes an electronic health records (EHR) database 104 that contains patient records. Electronic health records are a digital version of a patient's paper chart. The EHR database 104 can contain more information than a traditional patient chart, including, but not limited to, a patient's medical history, diagnoses, medications, treatment plans, allergies, diagnostic imaging, lab results, etc. In some embodiments, the steps for each procedure being performed on the patient in the operating room 116 are stored in the EHR database 104. Electronic health records can also include data collected from the sensors 118 from historical procedures. The EHR database 104 is implemented using components of the example computer system 900 illustrated and described in more detail with reference to FIG. 9.

In some embodiments, the EHR database 104 is a digital record of a patient's health information, collected and stored systematically over time. The EHR database 104 can include demographics, medical history, history of present illness (HPI), progress notes, problems, medications, vital signs, immunizations, laboratory data, or radiology reports. Software operating on the patient monitoring network 102 or implemented on the example computer system 900 (e.g., the instructions 904, 908 illustrated and described in more detail with reference to FIG. 9) is used to capture, store, and share patient data in a structured way. The EHR database 104 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 104 can also be used to facilitate clinical research by combining patients' demographics into a large pool. For example, the EHR database 104 can support a wide range of epidemiological research on the natural history of disease, drug utilization, and safety, as well as health services research.

The patient monitoring network 102 includes a threshold database 106 that contains data collected from the sensors 118 during an active surgical procedure and threshold values for the data collected that indicate an adverse event. The threshold database 106 is implemented using components of the example computer system 900 illustrated and described in more detail with reference to FIG. 9. For example, to avoid hypothermia, a patient's body temperature should be kept at or above 36.0° C. The threshold database 106 can also contain the output of a trend module 112 related to the rate of change in a given sensor data measurement over time and the amount of time before an alert threshold is reached at a present rate of change. The threshold database 106 can also contain information related to similar surgical procedures.

The patient monitoring network 102 includes a base alert module 108, which is implemented using components of the example computer system 900 illustrated and described in more detail with reference to FIG. 9. The base alert module 108 monitors the sensors 118 for new data events. The base alert module 108 includes a trend module 112. The trend module 112 is implemented using components of the example computer system 900 illustrated and described in more detail with reference to FIG. 9. The trend module 112 can be prompted to calculate a rate of change for the present sensor data values to determine if they will exceed one or more alert thresholds before the present surgical procedure is complete. In some embodiments, the trend module 112 determines the rate of change for data from the sensors 118 and the time until a sensor data value will exceed an alert threshold at the present rate of change.

The base alert module 108 includes a correlation module 114. The correlation module 114 is implemented using components of the example computer system 900 illustrated and described in more detail with reference to FIG. 9. The stored sensor data patterns are analyzed by the correlation module 114 as correlated to the sensor data patterns observed in the present surgical procedure. The correlation module 114 determines a number or proportion of the identified similar surgical procedures that resulted in an adverse event. The number or proportion can also be recorded in the threshold database 106. The correlation module 114 can be prompted to identify similar surgical procedures (e.g., within the EHR database 104 or the threshold database 106) having sensor data patterns that are correlated to the present surgical procedure's sensor data patterns, and identify any adverse events associated with the identified correlated procedures. In some embodiments, the correlation module 114 identifies previous surgical procedures similar to the present surgical procedure. The correlation module 114 can compare the patterns of sensor data over time to the sensor data over time being observed in the present patient to identify correlated procedures from those identified similar procedures. The number of those procedures associated with an adverse event can also be identified.

The base alert module 108 includes an alert condition module 110. The alert condition module 110 is implemented using components of the example computer system 900 illustrated and described in more detail with reference to FIG. 9. New data events prompt the alert condition module 110 to determine if the present sensor data values exceed a threshold in the threshold database 106 or if that sensor data value is proximate to an alert threshold value. In some embodiments, the alert condition module 110 compares present data values from the one or more sensors 118 to alert threshold values known in the art for a given sensor data type. For example, when a patient's body temperature drops below 36.0° C., indicating potential hypothermia, a value below that can prompt an alert or notification to the operating room 116. The alert condition module 110 can also identify sensor data values proximate, but not exceeding, alert thresholds.

The base alert module 108 delivers an alert to a surgeon through an interface 120 if one or more alert thresholds have been exceeded. The interface 120 is communicatively coupled to the sensors 118 and the patient monitoring network 102. The interface 120 is implemented using components of the example computer system 900 illustrated and described in more detail with reference to FIG. 9. The interface 120 can be a computing device, such as a computer, tablet, smartphone, smart speaker, etc., which is communicatively coupled to the patient monitoring network 102. Through the interface 120, the operating room 116 receives alerts from the base alert module 108. When no alert threshold has been exceeded, the base alert module 108 can still alert the operating room 116 if one of several conditions is met. An alert can be issued, in one or more embodiments, if at least two sensor values are proximate to an alert threshold, even if neither value exceeds the alert threshold. For example, a patient's body temperature can be 36.1° C., and their diastolic blood pressure can be 55 mm Hg. Neither exceeds standard alert thresholds known in the art, but both are within 10% of their respective alert thresholds. Since both values are related to a condition of hypothermia in a patient, an alert can be sent to the operating room 116.

In some embodiments, an alert is communicated using high-definition monitors, which refer to displays in which a clearer picture is possible than with low-definition, low-resolution screens. High-definition monitors have a higher density of pixels per inch than past standard TV screens. Resolution for high-definition monitors may be 1280×720 pixels or more (e.g., Full HD, 1920×1080; Quad HD, 2560×1440; 4K, 3840×2160; 8K, 7680×4320 pixels). A high-definition monitor may operate in progressive or interlaced scanning mode. High-definition monitors used in medical applications may offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some additional embodiments, at least one monitoring sensor (e.g., 118a) receives sensor readings from a patient undergoing a surgical procedure. One or more processors of a surgical alert system (e.g., the patient monitoring network 102) analyze the sensor readings based on stored adverse event data from prior surgical procedures matching the surgical procedure (e.g., in threshold database 106 or the EHR database 104). The surgical alert system determines one or more patient-specific alert criteria based on analyzing the sensor readings. The surgical alert system determines whether at least one of the patient-specific alert criteria is met based on additional sensor readings from the at least one monitoring sensor 118a. Responsive to determining that the at least one of the patient-specific alert criteria is met, the surgical system generates an alert. In some embodiments, the received sensor readings include one or more physiological parameters of the patient. Analyzing the sensor readings includes correlating the one or more physiological parameters to the adverse event data.

In some embodiments, the surgical alert system (e.g., the patient monitoring network 102) monitors a physiological condition of the patient based on the received sensor readings. The surgical alert system determines a predicted time at which the physiological condition of the patient will meet a threshold physiological condition associated with an adverse surgical event based on a rate of change of the received sensor readings. Responsive to determining the predicted time, the surgical alert system transmits an alert to one or more robotic surgical controls of a robotic surgical system programmed to adjust one or more surgical steps prior to the predicted time. In some embodiments, the robotic surgical system is the same as or similar to the surgical system 122. In some embodiments, the surgical alert system receives a surgical plan that includes surgical steps. The surgical alert system compares the surgical steps to corresponding reference surgical steps of the prior surgical procedures. The surgical alert system identifies a set of the stored adverse event data from the corresponding reference surgical steps. The surgical alert system identifies the surgical steps for specific alerts based on the set of the stored adverse event data. The surgical alert system determines one or more patient-specific alert thresholds for each of the identified surgical steps for specific alerts. In some embodiments, the surgical alert system uses at least one machine-learning model 712 to determine the one or more patient-specific alert criteria based on analyzing the sensor readings. The machine-learning model 712 is illustrated and described in more detail with reference to FIG. 7.

In some embodiments, analyzing the sensor readings includes comparing, by the surgical alert system, patterns in the stored adverse event data to the received sensor readings using at least one of convolution, auto-correlation, or cross-correlation. In some embodiments, analyzing the sensor readings includes comparing, by the surgical alert system, one or more physiological parameters of the patient to stored electronic health records (e.g., the EHR database 104) associated with the stored adverse event data using regression analysis. In some embodiments, the at least one monitoring sensor 118a includes at least one of a heart-rate monitor, a pulse oximeter, a capnography monitor, a blood pressure monitor, a body temperature monitor, or an electrocardiogram machine. In some embodiments, the surgical alert system determines one or more potential future adverse events for the surgical procedure. The surgical alert system determines a predicted outcome of the respective one or more potential future adverse events. The surgical alert system determines at least one patient-specific threshold for the one or more patient-specific alert criteria based on the predicted outcome.

In some embodiments, the surgical alert system determines a patient-specific monitoring alert plan based on patient data collected prior to beginning the surgical procedure. In response to monitoring the patient, the surgical alert system adjusts the patient-specific monitoring alert plan. In some embodiments, the surgical alert system classifies the alert as a critical patient alert, a predicted adverse event alert, or a modify procedure alert.

In some embodiments, a surgical monitoring network (e.g., the patient monitoring network 102) receives sensor readings from a patient during surgery. One or more processors of the surgical monitoring network identify one or more patterns in the sensor readings based on stored electronic health records (e.g., in the EHR database 104) and correlations to potential adverse events. The surgical monitoring network determines at least one alert threshold for monitoring the patient based on the identified one or more patterns. In some embodiments, the surgical monitoring network determines one or more actions responsive to the sensor readings meeting the at least one alert threshold. In some embodiments, the sensor readings correspond to one or more physiological parameters of the patient. The surgical monitoring network correlates the one or more physiological parameters to adverse event data from the stored electronic health records. The adverse event data is associated with prior surgeries matching the surgery. In some embodiments, the surgical monitoring network monitors a physiological condition of the patient based on the sensor readings. The surgical monitoring network determines a predicted time at which the physiological condition of the patient will meet a threshold physiological condition associated with an adverse surgical event based on a rate of change of the one or more physiological parameters. Responsive to determining the predicted time, the surgical monitoring network transmits an alert to a surgical system 122 performing at least a portion of the surgery. The surgical system 122 is programmed to adjust the surgery prior to the predicted time.

In some embodiments, the surgical monitoring network receives a surgical plan including surgical steps to be performed. The surgical monitoring network compares the surgical steps to prior surgical steps from the stored electric health records. The surgical monitoring network identifies stored adverse event data from the prior surgical steps matching the surgical steps to be performed based on the comparison. In some embodiments, the surgical monitoring network uses at least at one machine-learning model 712 to determine when to adjust the at least one alert threshold. In some embodiments, the surgical monitoring network compares patterns in the potential adverse events to the received sensor readings using at least one of convolution, auto-correlation, or cross-correlation. In some embodiments, the surgical monitoring network compares one or more physiological parameters of the patient to stored electronic health records using regression analysis. In some embodiments, the sensor readings are from at least one of a heart-rate monitor, a pulse oximeter, a capnography monitor, a blood pressure monitor, a body temperature monitor, or an electrocardiogram machine. In some embodiments, the surgical monitoring network determines one or more potential future adverse events for the surgery. The surgical monitoring network determines a predicted outcome of the one or more potential future adverse events.

In some embodiments, the surgical monitoring network determines a patient-specific monitoring alert plan based on patient data collected prior to beginning the surgery. In response to monitoring the patient, the surgical monitoring network adjusts the patient-specific monitoring alert plan based the received sensor data. In some embodiments, the surgical monitoring network generates an alert classified as a critical alert or a non-critical alert. In some embodiments, the surgical monitoring network generates at least one of a critical patient alert, a predicted adverse event alert, or a modify procedure alert.

In some embodiments, the adaptive patient condition surgical warning system 100 or the patient monitoring network 102 uses quantum computing. Quantum computing refers to a computational device or method that utilizes properties of quantum states defined by quantum mechanics such as superposition, entanglement, etc., to perform computations. Quantum devices utilize qubits which are the quantum equivalent to bits in a classical computing system. Qubits include at least two quantum states or probable outcomes. These outcomes, combined with a coefficient representing the probability of each outcome, describe the possible states, or bits of data, which can be represented by the qubits according to the principle of quantum superposition. These states can be manipulated which can shift the probability of each outcome or additionally add additional possible outcomes to perform a calculation, the final state of which can be measured to achieve a result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that the nature of quantum computing is the same as the systems being simulated. In medical fields, quantum computing shows great promise for drug discovery and simulating the interaction of drugs with biologic systems, however, the same technology can be used to predict the interaction of a biologic system with an implanted device, preventing rejection of an implant by a patient's body, long term function of an implant, and potentially the reaction of a patient to a surgical procedure during a simulation before a procedure or actively during a procedure.

FIG. 2 illustrates an example threshold database 106, in accordance with one or more embodiments. The threshold database 106 is also illustrated and described in more detail with reference to FIG. 1. The threshold database 106 contains data measurements related to the present surgical procedure from one or more of the sensors 118. The sensors 118 are illustrated and described in more detail with reference to FIG. 1. The threshold database 106 can include data from patient monitoring equipment such as pulse oximeters, thermometers, EKGs, blood pressure monitors, etc. The threshold database 106 can include data related to a surgical procedure's context, such as a temperature of the operating room 116 or the rate of delivery of anesthesia. The operating room 116 is illustrated and described in more detail with reference to FIG. 1.

In some embodiments, in addition to recent sensor 118 measurements, the threshold database 106 can include a history of data measurements during the present surgical procedure. Alert thresholds, e.g., defined by regulatory bodies, medical facilities, device manufacturers, etc., or accepted practices, can be stored in the threshold database 106 to allow the alert condition module 110 to identify if a sensor 118 value indicates an alert condition. The alert condition module 110 is illustrated and described in more detail with reference to FIG. 1. The data collected over time during a surgical procedure can be used by the trend module 112 to identify the rate of change in a given variable being measured. The trend module 112 is illustrated and described in more detail with reference to FIG. 1. Until a variable crosses an alert condition threshold, it can be stored in the threshold database 106. Surgical procedures in the EHR database 104 that are identified, by the correlation module 114, as similar to the present surgical procedure and a number or proportion of those surgical procedures associated with an adverse event can also be stored in the threshold database 106. The EHR database 104 and correlation module 114 are illustrated and described in more detail with reference to FIG. 1.

Figure 3:
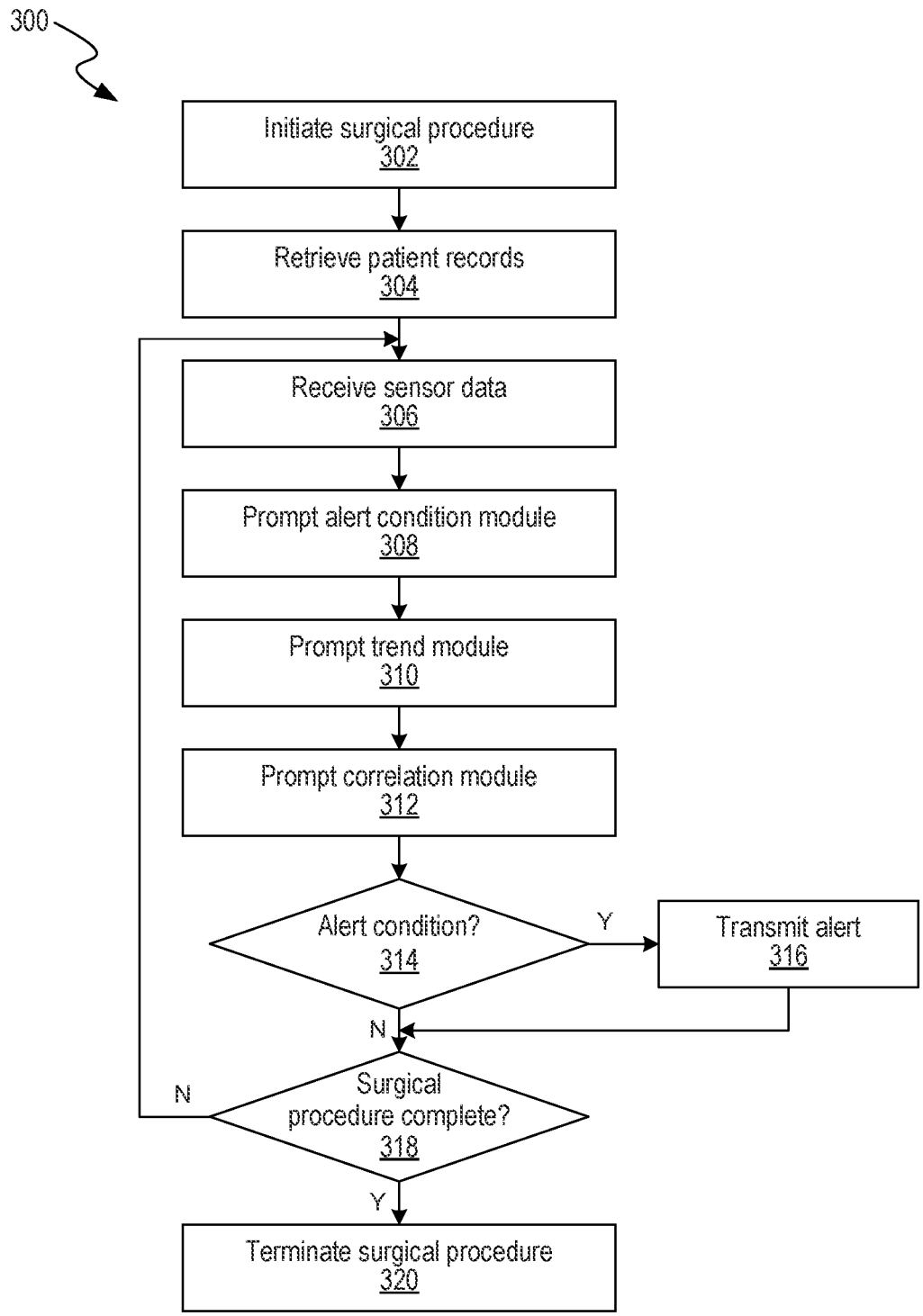
FIG. 3 is a flow diagram illustrating an example process performed by a base alert module, in accordance with one or more embodiments.

FIG. 3 is a flow diagram illustrating an example process 300 performed by the base alert module 108, in accordance with one or more embodiments. The base alert module 108 is illustrated and described in more detail with reference to FIG. 1. In other embodiments, the process 300 of FIG. 3 is performed by a computer system, e.g., the example computer system 900 illustrated and described in more detail with reference to FIG. 9. Particular entities, for example, the patient monitoring network 102, perform some or all of the steps of the process in other embodiments. Likewise, embodiments may include different and/or additional steps, or perform the steps in different orders. The patient monitoring network 102 is illustrated and described in more detail with reference to FIG. 1.

In step 302, a base alert module 302 receives a message that a surgeon and/or a robotic surgical system has initiated the surgical procedure. In some embodiments, the robotic surgical system is the same as or similar to the surgical system 122 illustrated and described in more detail with reference to FIG. 1. In some embodiments, the robotic surgical system provides intelligent services and information to the operating room 116 and the patient monitoring network 102 by interacting with the environment, including human beings, via the use of various sensors, actuators, and human interfaces. The operating room 116 is illustrated and described in more detail with reference to FIG. 1. The robotic surgical system is employed for automating processes in a wide range of applications, ranging from industrial (manufacturing), domestic, medical, service, military, entertainment, space, etc. The medical robotic system market can be segmented by product type into surgical robotic systems, rehabilitative robotic systems, non-invasive radio-surgery robotic systems, and hospital and pharmacy robotic systems. Robotic surgeries are performed using tele-manipulators, which use the surgeon's actions on one side to control one or more "effectors" on the other side. A medical robotic system ensures precision and can be used for remotely controlled, minimally invasive procedures. The systems include computer-controlled electromechanical devices that work in response to controls manipulated by the surgeons.

In step 304, the base alert module 108 retrieves medical records related to the patient undergoing the present surgical procedure from the EHR database 104. The EHR database 104 is illustrated and described in more detail with reference to FIG. 1. In step 306, the base alert module receives sensor data from the one or more sensors 118. The one or more sensors 118 are illustrated and described in more detail with reference to FIG. 1. The sensors 118 can return measurement data related to the patient, such as heart rate, blood pressure, blood oxygen level, body temperature, etc. The sensors 118 can also return data related to the context of the surgical procedure, such as the operating room 116 temperature, surgical procedure step, surgical supplies in use, equipment settings, etc. An example is the anesthesia delivery levels and timing.

In some embodiments, the surgical supplies include consumables or necessary supplies for the health system to provide care within the hospital or surgical environment. Consumables can include gloves, gowns, masks, syringes, needles, sutures, staples, tubing, catheters, or adhesives for wound dressing, in addition to other tools needed by doctors and nurses to provide care. Depending on the device, mechanical testing can be carried out in tensile, compression or flexure; in dynamic or fatigue; via impact; or with the application of torsion. Consumables can be disposable (e.g., time-saving, have no risk of healthcare-associated infections, and cost-efficient) or sterilizable (to avoid cross-contamination or risk of surgical site infections).

After data is received from the sensors 118 in step 306, the base alert module 108 prompts the alert condition module 110 in step 308. The alert condition module 110 is illustrated and described in more detail with reference to FIG. 1. The alert condition module 110 identifies any alert thresholds that the present sensor data has exceeded or is proximate to. In step 310, the base alert module 108 prompts the trend module 112. The trend module 112 is illustrated and described in more detail with reference to FIG. 1. The trend module 112 identifies the present sensor data trend.

In step 312, the base alert module 108 prompts the correlation module 114. The correlation module 114 is illustrated and described in more detail with reference to FIG. 1. The correlation module 114 identifies similar historical surgical procedures having correlated sensor patterns to the present sensor data. In some embodiments, the correlation module 114 indicates an alert condition when patterns of one or more sensor measurements are correlated with similar surgical procedures during which an adverse event occurred in at least a given absolute number of previous cases or in at least a given percentage of previous cases. For example, a pattern of blood pressure measurements over time for the present patient can be correlated to blood pressure measurements of 50 other patients who underwent a similar surgical procedure, who may have one or more shared characteristics with the present patient. In some embodiments, the correlation module 114 indicates an alert when 10% of the 50 identified patients experience an adverse event. In some embodiments, a threshold for an alert condition can be an absolute number, such as 5 previous surgeries having an adverse event.

The base alert module 108 determines, in step 314, if an alert condition is present and should be signaled. In some embodiments, the base alert module 108 generates an alert when one or more alert thresholds are identified by the alert condition module 110, for example, if the patient's body temperature has dropped below 36.0° C., or their diastolic blood pressure is 55 mm Hg. In some embodiments, the base alert module 108 generates an alert when the trend module 112 identifies a present non-alert condition sensor value that can cross an alert condition threshold in a given amount of time, based on at least two measurements over time of that sensor value for the present surgical procedure. For example, a patient's diastolic blood pressure can be 55 mm Hg, which is not beyond the alert threshold of 50 mm Hg. However, this is the third measurement of the patient's diastolic blood pressure: 60 mm Hg 10 minutes ago, and 57 mm Hg 5 minutes ago. The trend module 112 determines that the patient's diastolic blood pressure will exceed the threshold in 10 minutes if the present rate of change remains constant.

In some embodiments, the base alert module 108 determines that the surgical procedure will complete before the patient's diastolic blood pressure exceeds the alert threshold. In such a case, the base alert module 108 does not generate an alert. In another case, the base alert module 108 can generate an alert if the present surgical procedure is predicted by the base alert module 108 to take more than 10 more minutes. In some embodiments, the base alert module 108 generates an alert when at least two measurements from the sensors 118 are identified as proximate to an alert threshold by the alert condition module 110, for example, if the patient's body temperature is 36.3° C., and their diastolic blood pressure is 55 mm Hg. Neither of these values is beyond the standard thresholds known in the art: 36.0° C. and 50 mm Hg, respectively. In traditional patient monitoring systems, these values would not trigger an alert to the operating room 116. In some embodiments, when both values are within 10% of the alert thresholds, the base alert module 108 generates an alert because the patient can be approaching a hypothermia condition.

If an alert condition is identified by the base alert module 108 in step 310, the alert can be transmitted in step 316 to the operating room 116, a surgeon, a nurse, an anesthesiologist, etc. The alert can be delivered in different ways, including, but not limited to, an audible alert, text displayed on the interface 120, spoken words delivered by a voice assistant, or haptic feedback through robotic surgical controls. The interface 120 is illustrated and described in more detail with reference to FIG. 1. Patients under anesthesia for a surgical procedure require careful monitoring, as anesthesia and surgery can cause rapid changes in vital functions. Anesthesia impacts the function of the central nervous, cardiovascular, and respiratory systems. The American Society of Anesthesiologists (ASA) has a standard set of monitoring devices, which may include a pulse oximeter, electrocardiogram, temperature probe, blood pressure cuff, etc. The gas exchange of a patient's inhaled and exhaled breath may also be monitored through the anesthesia machine. This equipment is used to titrate anesthetic medication administration, detect physiologic perturbations, allow intervention before the patient suffers harm, and detect and correct equipment malfunction.

In some embodiments, the robotic surgical controls include a surgical tower for minimally invasive surgery (MIS). A surgical tower includes instruments used for performing MIS or surgery which is performed by creating small incisions in the body. The instruments are also referred to as minimally invasive devices or minimally invasive access devices. The procedure of performing MIS may also be referred to as a minimally invasive procedure. MIS is a safe, less invasive, and more precise surgical procedure. Some of the advantages offered by surgical towers may be small incisions, less pain, low risk of infection, short hospital stays, quick recovery time, less scarring, and reduced blood loss. Some medical procedures where surgical towers are useful and are widely used may be procedures for lung, gynecological, head and neck, heart, and urological conditions. MIS may be robotic or non-robotic/endoscopic. MIS may include endoscopic, laparoscopic, arthroscopic, natural orifice intraluminal, and natural orifice transluminal procedures. A surgical tower access device may be designed as an outer sleeve and an inner sleeve that telescopingly or slidably engages with one another. When a telescope is used to operate on the abdomen, the procedure is called laparoscopy. Surgical towers typically include access to a variety of surgical tools, such as, for example, electrocautery, radiofrequency, lasers, sensors, etc. A surgical tower can be integrated into the embodiments in a variety of manners.

Electrocautery is performed by an instrument used for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision, an electrocautery instrument can be used. For example, after removing part of the liver for removal of a tumor, etc., blood vessels in the liver must be sealed individually. An electrocautery instrument can be used for sealing living tissue such as arteries, veins, lymph nodes, nerves, fats, ligaments, and other soft tissue structures. It may be used in applications such as surgery, tumor removal, nasal treatment, or wart removal. Electrocautery may operate in two modes: monopolar or bipolar. The electrocautery instrument may consist of a generator, a handpiece, and one or more electrodes.

In some embodiments, radiofrequency (RF) is used in association with MIS devices. The RF may be used for the treatment of skin by delivering it to the skin through a minimally invasive tool (e.g., fine needles), which does not require skin excision. The RF may be used for real-time tracking of MIS devices such as laparoscopic instruments. The RF may provide radiofrequency ablation to a patient suffering from atrial fibrillation through smaller incisions made between the ribs. The RF may be used to perform an endoscopic surgery on the body, such as the spine, by delivery of RF energy.

In some embodiments, a laser is used in association with MIS devices. The laser may be used in MIS with an endoscope. The laser is attached to the distal end of the endoscope and steers the laser at high speed by producing higher incision quality than with existing surgical tools and minimizing damage to surrounding tissue. Lasers may be used to perform MIS using a laparoscope in the lower and upper gastrointestinal tract, eye, nose, and throat. Lasers are used in MIS to ablate soft tissues, such as a herniated spinal disc bulge.

In some embodiments, sensors are used in association with MIS devices. The sensor may be used in MIS for tactile sensing of tool—tissue interaction forces. During MIS, the field of view and workspace of tools are compromised due to the indirect access to the anatomy and lack of the surgeon's hand-eye coordination. The sensors provide a tactile sensation to the surgeon by providing information of shape, stiffness, and texture of organ or tissue (different characteristics) to the surgeon's hands through a sense of touch. This detection of a tumor through palpation exhibits a 'tougher' feel than healthy soft tissue, pulse felt from blood vessels, and abnormal lesions. The sensors may output shape, size, pressure, softness, composition, temperature, vibration, shear, and normal forces. Sensors may be electrical or optical, consisting of capacitive, inductive, piezoelectric, piezoresistive, magnetic, and auditory. The sensors may be used in robotic or laparoscopic surgery, palpation, biopsy, heart ablation, and valvuloplasty.

In some embodiments, imaging systems or instruments are used for the creation of images and visualization of the interior of a human body for diagnostic and treatment purposes. Imaging systems are used in different medical settings and can help in the screening of health conditions, diagnosing causes of symptoms, or monitoring of health conditions. Imaging systems may include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which may drive the market are cost and clinical advantages of medical imaging modalities, a rising share of aging populations, increasing prevalence of cardiovascular or lifestyle diseases, and increasing demand from emerging economies. Some factors which may inhibit the market are saturation in many segments, high costs, or lack of trained personnel.

In some embodiments, X-ray medical imaging instruments that use X-ray radiation (i.e., X-ray range in the electromagnetic radiation spectrum) for the creation of images of the interior of the human body for diagnostic and treatment purposes are used. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used may be bone fractures, infections, calcification, tumors, arthritis, blood vessel blockages, digestive problems, or heart problems. The X-ray instrument may consist of components such as an X-ray tube, operating console, collimator, grid, detector, radiographic film, etc.

In some embodiments, MRI medical imaging instruments that use powerful magnets for the creation of images of the interior of the human body for diagnostic and treatment purposes are used. Some of the applications where MRI may be used may be brain/spinal cord anomalies, tumors in the body, breast cancer screening, joint injuries, uterine/pelvic pain detection, or heart problems. For the creation of the image by an MRI instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI may be more widely suited for imaging of non-bony parts or soft tissues of the body. MRI may be less harmful, as it does not use damaging ionizing radiation as in the X-ray instrument. MRI instruments may consist of magnets, gradients, radiofrequency systems, or computer control systems. Some areas where imaging by MRI should be prohibited may be people with implants.

In some embodiments, computed tomography imaging (CT) that uses an X-ray radiation (i.e., X-ray range in the electromagnetic radiation spectrum) for the creation of cross-sectional images of the interior of the human body is used. CT refers to a computerized X-ray imaging procedure in which a narrow beam of X-rays is aimed at a patient and quickly rotated around the body, producing signals that are processed by the machine's computer to generate cross-sectional images—or "slices"—of the body. A CT instrument is different from an X-ray instrument as it creates 3-dimensional cross-sectional images of the body, while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient, shooting narrow beams of X-rays through the body. Some of the applications where CT may be used may be blood clots; bone fractures, including subtle fractures not visible on X-ray; or organ injuries.

In some embodiments, stereotactic navigation systems that use patient imaging (e.g., CT, MRI) to guide surgeons in the placement of specialized surgical instruments and implants are used. The patient images are taken to guide the physician before or during the medical procedure. The stereotactic navigation system includes a camera having infrared sensors to determine the location of the tip of the probe being used in the surgical procedure. This information is sent in real-time so that the surgeons have a clear image of the precise location of where they are working in the body. Stereotactic navigation systems may be framed (require attachment of a frame to the patient's head using screws or pins) or frameless (do not require the placement of a frame on the patient's anatomy). Stereotactic navigation systems may be used for diagnostic biopsies, tumor resection, bone preparation/implant placement, placement of electrodes, otolaryngologic procedures, or neurosurgical procedures.

In some embodiments, ultrasound imaging, also referred to as sonography or ultrasonography, that uses ultrasound or sound waves (also referred to as acoustic waves) for the creation of cross-sectional images of the interior of the human body is used. Ultrasound in the instrument may be produced by a piezoelectric transducer, which produces sound waves and sends them into the body. The sound waves that are reflected are converted into electrical signals which are sent to an ultrasound scanner. Ultrasound instruments may be used for diagnostic and functional imaging or for therapeutic or interventional procedures. Some of the applications where ultrasound may be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound may be used for internal imaging (where the transducer is placed in organs, e.g., vagina) and external imaging (where the transducer is placed on the chest for heart monitoring or the abdomen for the fetus). An ultrasound machine may consist of a monitor, keyboard, processor, data storage, probe, and transducer.

In some embodiments, the system 100 uses endoscopes, arthroscopes, or laparoscopes for MIS techniques where procedures are performed by performing a minimal incision in the body. An endoscope refers to an instrument used to visualize, diagnose, and treat problems inside hollow organs where the instrument is inserted through natural body openings such as the mouth or anus. An endoscope may perform a procedure as follows: a scope with a tiny camera attached to a long, thin tube is inserted. The doctor moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope may perform the procedure as follows: a surgeon makes a small incision in a patient's skin and inserts a pencil-sized instrument with a small lens and lighting system to magnify the target site (joint) and viewing of the interior of the joint by means of a miniature TV camera, and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 uses fiber optics, which refer to flexible, transparent fiber made by drawing glass (silica) or plastic to a diameter slightly thicker than that of a human hair. Fiber optics are arranged in bundles called optical cables and used to transmit light signals over long distances. Fiber optics are used most often as a means to transmit light between the two ends of the fiber and find wide usage in the medical field. Traditional surgery requires sizable and invasive incisions to expose internal organs and operate on affected areas, but with fiber optics, much smaller surgical incisions can be performed. Fiber optics contain components such as a core, cladding, and buffer coating. Fiber optics may be inserted in hypodermic needles and catheters, endoscopes, operation theatre tools, ophthalmological tools, and dentistry tools. Fiber optic sensors comprise a light source, optical fiber, external transducer, and photodetector. Fiber optic sensors may be intrinsic or extrinsic. Fiber optic sensors may be categorized into four types: physical, imaging, chemical, and biological.

In some embodiments, the system 100 uses surgical lights (referred to as operating lights), which refer to an instrument that performs illumination of a local area or cavity of the patient. Surgical lights play an important role in illumination before, during, and after a medical procedure. Surgical lights may be categorized by lamp type as conventional (incandescent) and LED (light-emitting diode). Surgical lights may be categorized by mounting configuration as ceiling-mounted, wall-mounted, or floor stand. Surgical lights may be categorized by type as tungsten, quartz, and/or xenon halogens and light-emitting diodes (LEDs). Surgical lights include sterilizable handles, which allow the surgeon to adjust light positions. Some important factors affecting surgical lights may be illumination, shadow management (cast shadows and contour shadows), the volume of light, heat management, or fail-safe surgical lighting.

In step 318, the base alert module 108 determines whether the surgical procedure is complete. In some embodiments, one or more of the sensors 118 can indicate to the patient monitoring network 102 that the procedure is complete. For example, a microphone can receive verbal confirmation from a surgeon or a nurse that the procedure is complete. In other embodiments, an image recognition system in the operating room 116 can identify a condition or position of certain objects, personnel, or the patient. For example, the condition can be captured in images by operating room cameras that collect images from 360° or sensors that monitor both the operating room 116 and the people in it. Operating room cameras can include cameras in situ that perform recordings to give a bird's-eye view to the surgical team. Some cameras are on devices that surgeons insert through small incisions or orifices to see what they are doing during minimally invasive surgery (MIS). Operating room cameras can record for educational purposes, such as to broadcast a live feed of a surgical demonstration to a remote audience; to collect authentic footage for edited, instructional videos on a surgical technique or procedure; to facilitate video enhanced debriefing and coaching; or to formally assess surgical skills. The base alert module 108 associates the condition of the operating room 116 captured in images with a final step in the present surgical procedure.

In step 318, if the procedure is not complete, the process 300 returns to step 306. If it is determined at step 318 that the surgical procedure is complete, the process 300 terminates in step 320.

Figure 4:
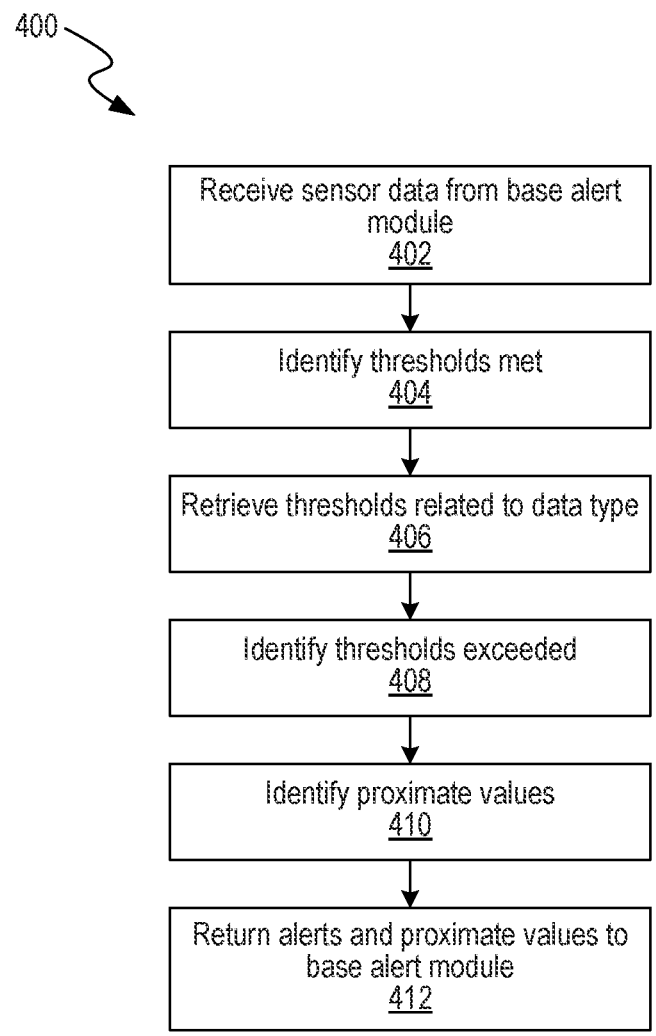
FIG. 4 is a flow diagram illustrating an example process performed by an alert condition module, in accordance with one or more embodiments.

FIG. 4 is a flow diagram illustrating an example process 400 performed by an alert condition module 110, in accordance with one or more embodiments. The alert condition module 110 is illustrated and described in more detail with reference to FIG. 1. In other embodiments, the process 400 of FIG. 4 is performed by a computer system, e.g., the example computer system 900 illustrated and described in more detail with reference to FIG. 9. Particular entities, for example, the patient monitoring network 102 or the base alert module 108, perform some or all of the steps of the process in other embodiments. Likewise, embodiments may include different and/or additional steps, or perform the steps in different orders. The patient monitoring network 102 and the base alert module 108 are illustrated and described in more detail with reference to FIG. 1.

In step 402, the alert condition module 110 receives a prompt from the base alert module 108 that there is sensor data available about the present surgical procedure from one or more of the sensors 118. The sensors 118 are illustrated and described in more detail with reference to FIG. 1. The alert condition module 110 receives the sensor data from the base alert module 108 or from the interface 120. In step 404, the alert condition module 110 identifies the type of sensor data received (e.g., from the base alert module 108). For example, the alert condition module 110 can receive sensor data describing a blood pressure, a pulse rate, a temperature, or other data from one or more of the sensors 118. In step 406, the alert condition module 110 retrieves threshold values for the sensor data related to the identified data type from the threshold database 106. The threshold database 106 is illustrated and described in more detail with reference to FIG. 1.

In step 408, the alert condition module 110 identifies any present sensor data that exceeds a threshold related to that data type. In some embodiments, the alert condition module 110 determines that a physiological condition of the patient has met a threshold physiological condition (e.g., hypothermia, elevated blood pressure, minimal pulse, etc.) based on the sensor data. Hypothermia is a potential adverse event connected to anesthesia. During surgery, the patient is exposed to a cold environment and has fluids that are typically colder than the patient's core body temperature being infused. The standard process of thermoregulation would typically be enough to overcome this, but that response can be compromised under anesthesia. Thus, temperature monitoring and perioperative thermoregulation methods are a critical part of the surgery. For example, a temperature sensor can return a patient body temperature of 35.8° C. The sensor data value has fallen below the lower body temperature threshold of 36.0° C. In some embodiments, responsive to determining that the physiological condition of the patient has met a threshold physiological condition, the alert condition module 110 or the base alert module 108 transmits an alert to one or more robotic surgical controls to terminate the surgery. This alert is sometimes referred to as a second alert because it can be transmitted after transmitting a first alert predicting an adverse event.

In step 410, the alert condition module 110 identifies sensor data values that do not exceed a threshold but are proximate to the threshold values for that data type. In some embodiments, the base alert module 108 or the alert condition module 110 transmits an alert to one or more robotic surgical controls responsive to at least two of the measured physiological parameters of the patient being proximate to threshold physiological parameters. This alert is sometimes referred to as a third alert because it can be generated after a first alert (e.g., indicating a predicted time at which a physiological condition of the patient will meet a threshold physiological condition associated with an adverse surgical event based on a rate of change of one or more physiological parameters) but before a second alert (e.g., indicating that a physiological condition of the patient has met a threshold physiological condition). The definition of "proximate" value can change and be determined by data type, surgical procedure type, patient history, practitioner, facility preferences, etc. In some embodiments, a proximate sensor data value is within 10% of a threshold value. For example, when a lower threshold for diastolic blood pressure is 50 mm Hg, a sensor data value of less than 55 (50×1.10) mm Hg can be considered a proximate value. In step 412, the alert condition module 110 transmits the identified alert conditions and sensor data values proximate to the alert condition thresholds to the base alert module 108.

Figure 5:
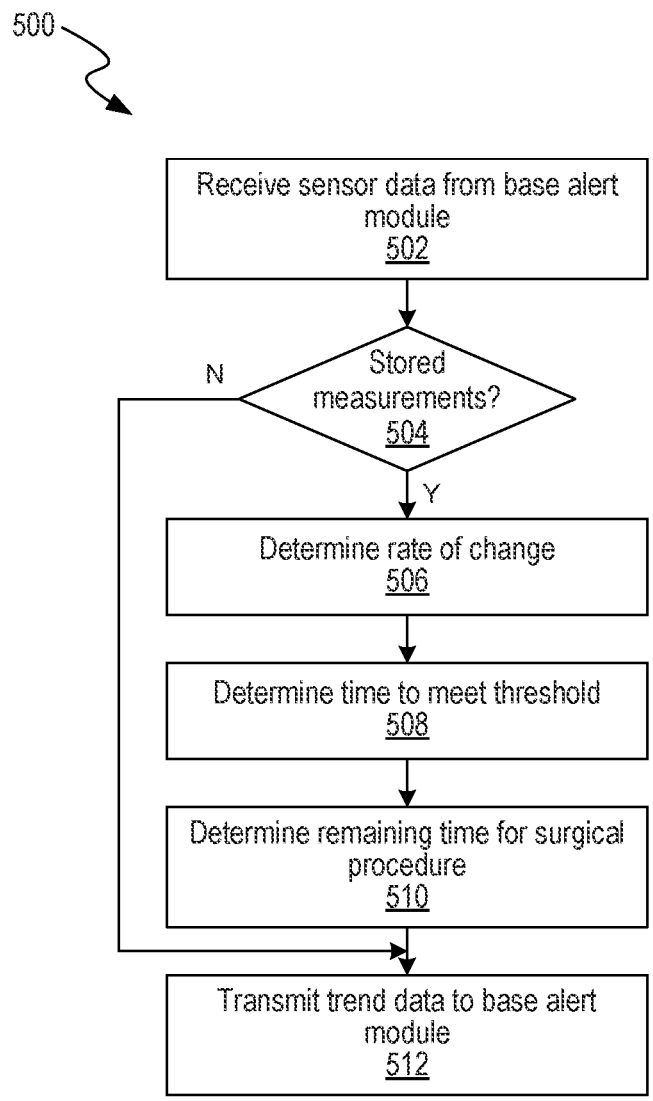
FIG. 5 is a flow diagram illustrating an example process performed by a trend module, in accordance with one or more embodiments.

FIG. 5 is a flow diagram illustrating an example process 500 performed by a trend module 112, in accordance with one or more embodiments. The trend module 112 is illustrated and described in more detail with reference to FIG. 1. In other embodiments, the process 500 of FIG. 5 is performed by a computer system, e.g., the example computer system 900 illustrated and described in more detail with reference to FIG. 9. Particular entities, for example, the patient monitoring network 102 or the base alert module 108, perform some or all of the steps of the process in other embodiments. Likewise, embodiments may include different and/or additional steps, or perform the steps in different orders. The patient monitoring network 102 and the base alert module 108 are illustrated and described in more detail with reference to FIG. 1.

In step 502, the trend module 112 receives a prompt from the base alert module 108 that there is sensor data available describing the present surgical procedure from one or more of the sensors 118. The sensors 118 are illustrated and described in more detail with reference to FIG. 1. The trend module 112 receives the sensor data. In step 504, the trend module 112 determines whether there are previous measurements of the same data type for the present surgical procedure stored in the threshold database 106. The threshold database 106 is illustrated and described in more detail with reference to FIG. 1. If there is no previous measurement stored for the present sensor data type, the trend module 112 proceeds to step 512 because at least two data points are required to calculate a rate of change. In some embodiments, based on the type of sensor data, the number of stored previous measurements of the present data type can need to be more than two to calculate a rate of change more accurately. For example, the trend module 112 will not attempt to determine a rate of change until at least 5 measurements of a given variable have been taken, especially for measurements taken more frequently, such as blood oxygen level or pulse rate, which are more continuously monitored.

In step 506, if there are sufficient stored previous measurements of the same data type, the trend module 112 determines a rate of change for that data type. For example, a patient's temperature is taken 3 times in the present surgical procedure. The present measurement is, say, 36.3° C. A measurement of 36.4° C. was collected 5 minutes ago, and a measurement of 36.5° C. was collected 10 minutes ago. The rate of change in this example is determined by the trend module 112 as −0.1° C. every 5 minutes.

In step 508, the trend module 112 determines an amount of time it will take for the present data type to exceed one or more thresholds at the identified rate of change. In some embodiments, the trend module 112 determines a predicted time at which a physiological condition of the patient will meet a threshold physiological condition associated with an adverse surgical event based on a rate of change of one or more physiological parameters measured by the sensors 118a-n. In step 510, the trend module 112 determines an amount of time remaining in the present surgical procedure. In some embodiments, responsive to determining the predicted time, the trend module 112 or the base alert module 108 transmits an alert to one or more robotic surgical controls of the system 100 to adjust the surgery prior to the predicted time. The system 100 is illustrated and described in more detail with reference to FIG. 1. This alert is sometimes referred to as a "first alert" because it can be generated before the physiological condition of the patient actually meets the threshold physiological condition associated with the adverse surgical event. The surgical procedure can be modified or terminated by the surgeon or the robotic controls to avoid the threshold physiological condition and the adverse surgical event. For example, the patient can be cooled down if she is overheating, heart rate can be reduced, or another intervention can be applied. In step 512, the trend module 112 transmits the determined rate of change and the determined time until the present value crosses a threshold at that rate of change to the base alert module 108.

Figure 6:
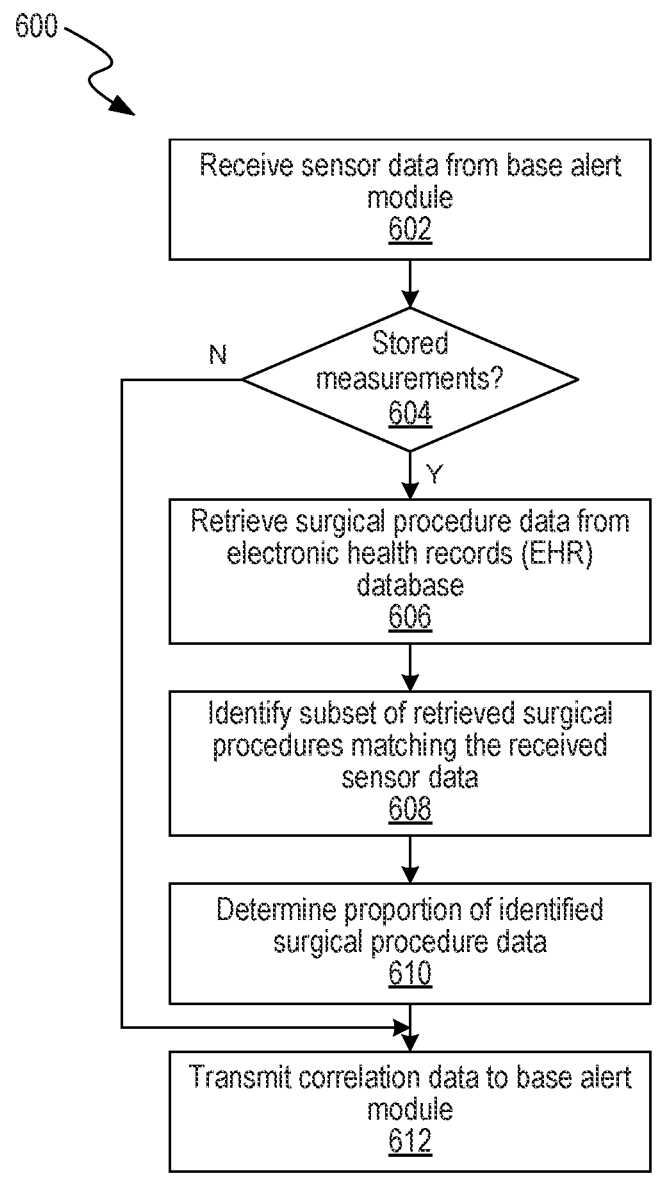
FIG. 6 is a flow diagram illustrating an example process performed by a correlation module, in accordance with one or more embodiments.

FIG. 6 is a flow diagram illustrating an example process performed by a correlation module 114, in accordance with one or more embodiments. The correlation module 114 is illustrated and described in more detail with reference to FIG. 1. In other embodiments, the process 600 of FIG. 6 is performed by a computer system, e.g., the example computer system 900 illustrated and described in more detail with reference to FIG. 9. Particular entities, for example, the patient monitoring network 102 or the base alert module 108, perform some or all of the steps of the process 600 in other embodiments. Likewise, embodiments may include different and/or additional steps, or perform the steps in different orders. The patient monitoring network 102 and the base alert module 108 are illustrated and described in more detail with reference to FIG. 1.

In some embodiments, the correlation module 114 correlates one or more measured physiological parameters of a patient to stored surgical data associated with one or more adverse surgical events. The one or more adverse surgical events are associated with surgical procedures matching or similar to the present surgery. For example, in step 602, the correlation module 114 receives a prompt from the base alert module 108 that there is sensor data available describing the present surgical procedure from one or more of the sensors 118. The sensors 118 are illustrated and described in more detail with reference to FIG. 1. The correlation module 114 receives the sensor data.

In some embodiments, correlating one or more measured physiological parameters of the patient to stored surgical data (e.g., in the EHR database 104 or the threshold database 106) includes identifying one or more adverse surgical events associated with previous surgical procedures matching the surgery using an electronic health record of the patient. In step 604, the correlation module 114 determines whether there are previous measurements of the same data type for the present surgical procedure stored in the threshold database 106. The threshold database 106 is illustrated and described in more detail with reference to FIG. 1. If there is no previous measurement stored for the present sensor data type, the correlation module 114 proceeds to step 612 because at least 2 data points are required to identify a pattern. In some embodiments, the number of stored previous measurements of the present sensor data type can need to be more than 2 to identify a pattern more accurately in the sensor data. For example, the correlation module 114 will not attempt to identify previous patients undergoing a similar surgical procedure who exhibited similar patterns of measurement of the present sensor data type being examined until 5 measurements of a given variable have been taken.

In step 606, the correlation module 114 retrieves records of similar surgical procedures from the EHR database 104. The EHR database 104 is illustrated and described in more detail with reference to FIG. 1. In some embodiments, a "similar surgical procedure" refers to a group of procedures, e.g., knee replacements. In other embodiments, a "similar surgical procedure" refers to a single surgical procedure, e.g., a partial right knee replacement, or, more specifically, a partial right knee replacement using a particular model of implant performed using a particular brand of robotic surgical system. In other embodiments, to qualify as "similar," a surgical procedure can need to include a common surgeon, anesthesiologist, or facility.

In step 608, the correlation module 114 identifies a subset of the similar surgical procedures having similar patterns of measurement for the present sensor data type. Identifying instances of similar patterns of sensor data can be done in several different ways. In some embodiments, correlating one or more measured physiological parameters of the patient to stored surgical data includes comparing patterns in the stored surgical data to the one or more physiological parameters using at least one of convolution, auto-correlation, or cross-correlation. In some embodiments, the correlation module 114 uses convolution, auto-correlation, or cross-correlation to compare the sensor data values from the present patient over time to the sensor data values over time in the identified similar surgical procedures. For example, a patient's blood pressure measurements over time can be expressed as a first function. For convolution, the function can be convolved against itself to identify an ideal function that results when a matching function of stored blood pressure measurements for a previous patient and a similar surgical procedure is convolved with the real-time sensor data from the present patient. The function of stored blood pressure measurements over time for each patient identified in step 608 is convolved with the first function. The resulting third function for each previous similar surgical procedure is compared to the ideal function. Comparing the two functions can be based on different factors, such as the area under the shape, slope, duty cycles, etc. A "similar pattern" can refer to a pattern that is within 10% of one or more of the measured variables.

In some embodiments, regression analysis is used to compare stored previous surgical procedure measurements with the present data. For example, stored partial right knee replacement procedure data in the EHR database 104 having patterns of blood pressure over time that have an R-value of at least 0.90 indicate that the two patterns are correlated. In step 610, the correlation module 114 identifies a percentage or proportion of the subset of similar surgical procedures associated with one or more adverse events. For example, regulatory bodies, such as the U.S. Food and Drug Administration, maintain databases of adverse events associated with surgical procedures through reporting requirements placed on medical device manufacturers, doctors, and medical facilities. Information related to adverse events can also be stored in and retrieved from the EHR database 104.

In some embodiments, the correlation module 114 correlates one or more measured physiological parameters of the patient to stored surgical data (e.g., in the EHR database 104 or the threshold database 106). The correlating includes comparing the one or more physiological parameters to stored electronic health records using regression analysis. The stored surgical data includes the stored electronic health records. For example, a present patient's blood pressure measurements are determined to be correlated to, say, 50 other partial right knee replacement patients' blood pressure measurement patterns because they each had a pattern of blood pressure measurements that resulted in an R-value of greater than 0.90 when compared using linear regression. Of those 50 correlated surgical procedures, 2 are associated with an adverse event.

In step 612, the correlation module 114 transmits such determined correlation data to the base alert module 108.

Figure 7:
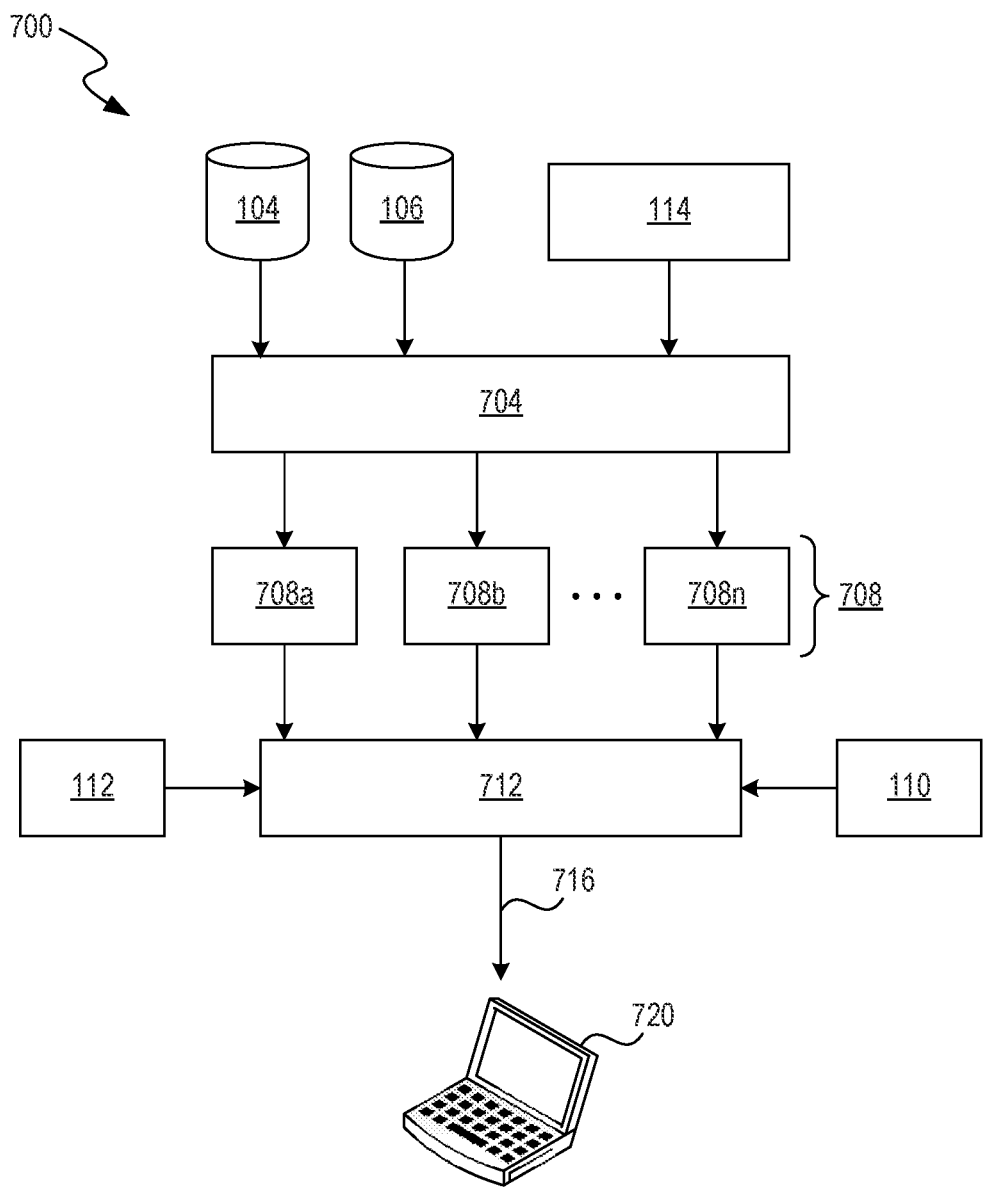
FIG. 7 is a block diagram illustrating an example machine learning system, in accordance with one or more embodiments.

FIG. 7 is a block diagram illustrating an example machine learning system 700, in accordance with one or more embodiments. The machine learning system 700 is implemented using components of the example computer system 900 illustrated and described in more detail with reference to FIG. 9. Likewise, embodiments of the machine learning system 700 may include different and/or additional components, or be connected in different ways. The machine learning system 700 is sometimes referred to as a machine learning module.

The machine learning system 700 includes a feature extraction module 704 implemented using components of the example computer system 900 illustrated and described in more detail with reference to FIG. 9. In some embodiments, the feature extraction module 704 extracts a feature vector 708 from one or more measured physiological parameters. For example, the measured physiological parameters can be stored in the EHR database 104 or the threshold database 106, or provided by the correlation module 114. The EHR database 104, the threshold database 106, and the correlation module 114 are illustrated and described in more detail with reference to FIG. 1.

The feature vector 708 is indicative of one or more adverse surgical events. The feature vector 708 includes features 708*a-n*. The feature extraction module 704 reduces the redundancy in data, e.g., repetitive data values, to transform the data into a reduced set of features, e.g., features 708*a*, 708*b*, 708*n*. The feature vector 708 contains the relevant information from the input data, such that adverse events or data value thresholds of interest can be identified by a machine learning model 712 by using this reduced representation. In some example embodiments, the following dimensionality reduction techniques may be used by the feature extraction module 704: independent component analysis, Isomap, kernel PCA, latent semantic analysis, partial least squares, principal component analysis, multifactor dimensionality reduction, nonlinear dimensionality reduction, Multilinear Principal Component Analysis, multilinear subspace learning, semidefinite embedding, Autoencoder, and deep feature synthesis.

In alternative embodiments, the machine learning model 712 may perform deep learning (also known as deep structured learning or hierarchical learning) to learn data representations, as opposed to using task-specific algorithms. In deep learning, no explicit feature extraction is performed; the features may be implicitly extracted by the machine learning system 700. For example, the machine learning model 712 may use a cascade of multiple layers of nonlinear processing units for implicit feature extraction and transformation. Each successive layer uses the output from the previous layer as input. The machine learning model 712 may thus learn in supervised (e.g., classification) and/or unsupervised (e.g., pattern analysis) modes. The machine learning model 712 may learn multiple levels of representations that correspond to different levels of abstraction, wherein the different levels form a hierarchy of concepts. In this manner, the machine learning model 712 may be configured to differentiate features of interest from background features.

The machine learning system 700 includes the machine learning model 712 implemented using components of the example computer system 900 illustrated and described in more detail with reference to FIG. 9. In some embodiments, correlating the one or more physiological parameters to stored surgical data includes identifying one or more adverse surgical events associated with previous surgical procedures matching the surgery using the machine learning model 712 based on the feature vector 708. The machine learning model 712 is previously trained based on the stored surgical data. The one or more adverse surgical events can be identified using data provided by the base alert module 108, the alert condition module 110, or the trend module 112.

In alternative example embodiments, the machine learning model 712 (in the form of a convolutional neural network) may generate an output, without the need for feature extraction, directly from data provided by the sensors 118*a-n*. The sensors 118*a-n* are illustrated and described in more detail with reference to FIG. 1. A CNN is a type of feed-forward artificial neural network in which the connectivity pattern between its neurons is inspired by the organization of a visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing. Advantages of CNNs include the obviation of feature extraction and the use of shared weight in convolutional layers, which means that the same filter (weights bank) is used for each pixel in the layer; this both reduces memory footprint and improves performance.

The machine learning model 712 may be a CNN that consists of both convolutional layers and max pooling layers. The architecture of the machine learning model 712 may be "fully convolutional," which means that variable sized sensor data vectors can be fed into it. For all convolutional layers, the machine learning model 712 may specify a kernel size, a stride of the convolution, and an amount of zero padding applied to the input of that layer. For the pooling layers, the machine learning model 712 may specify the kernel size and stride of the pooling.

In some embodiments, the machine learning system 700 trains the machine learning model 712, based on the stored surgical data, to correlate the physiological condition of the patient to the one or more adverse surgical events associated with the previous surgical procedures. As part of the training of the machine learning model 712, the machine learning system 700 forms a training set of features and training labels by identifying a positive training set of features that have been determined to have the property in question (e.g., sensor data proximate to a threshold value), and, in some embodiments, forms a negative training set of features that lack the property in question.

The machine learning system 700 may apply machine learning techniques to train the machine learning model 712 that, when applied to features, output indications of whether the features have an associated property or properties, such as probabilities that the features have a particular Boolean property, or an estimated value of a scalar property. The machine learning system 700 may apply dimensionality reduction (e.g., via linear discriminant analysis (LDA), principal component analysis (PCA), or the like) to reduce the amount of data in the feature vector 708 to a smaller, more representative set of data.

The machine learning system 700 may use supervised machine learning to train the machine learning model 712, with feature vectors of the positive training set and the negative training set serving as the inputs. In other embodiments, different machine learning techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., may be used. In some example embodiments, a validation set is formed of additional features, other than those in the training sets, which have already been determined to have or to lack the property in question. The machine learning system 700 applies the trained machine learning model 712 to the features of the validation set to quantify the accuracy of the machine learning model 712. Common metrics applied in accuracy measurement include: Precision and Recall, where Precision refers to a number of results the machine learning model 712 correctly predicted out of the total it predicted, and Recall refers to a number of results the machine learning model 712 correctly predicted out of the total number of features that did have the property in question. In some embodiments, the machine learning system 700 iteratively re-trains the machine learning model 712 until the occurrence of a stopping condition, such as the accuracy measurement indication that the machine learning model 712 is sufficiently accurate, or a number of training rounds, has taken place.

FIG. 8 is a flow diagram illustrating an example process 800 for an adaptive patient condition surgical warning system 100, in accordance with one or more embodiments. The adaptive patient condition surgical warning system 100 is illustrated and described in more detail with reference to FIG. 1. In other embodiments, the process 800 of FIG. 8 is performed by a computer system, e.g., the example computer system 900 illustrated and described in more detail with reference to FIG. 9. Particular entities, for example, the patient monitoring network 102 or the base alert module 108, perform some or all of the steps of the process 800 in other embodiments. Likewise, embodiments may include different and/or additional steps, or perform the steps in different orders. The patient monitoring network 102 and the base alert module 108 are illustrated and described in more detail with reference to FIG. 1.

One or more monitoring devices (e.g., sensors 118*a-n*) of a surgical system monitor (804) one or more physiological parameters of a patient undergoing surgery. The surgical system is the same as or similar to the adaptive patient condition surgical warning system 100. The sensors 118*a-n* are illustrated and described in more detail with reference to FIG. 1. The one or more physiological parameters (e.g., respiratory rate, blood pressure, blood oxygen level, heart rate, etc.) describe a physiological condition of the patient.

One or more processors of the surgical system correlate (808) the one or more physiological parameters to stored surgical data associated with one or more adverse surgical events. The stored surgical data can be the EHR database 104 and/or the threshold database 106 illustrated and described in more detail with reference to FIG. 1. The one or more adverse surgical events are associated with surgical procedures matching the surgery. In some embodiments, correlating the one or more measured physiological parameters of the patient to the stored surgical data includes comparing patterns in the stored surgical data to the one or more physiological parameters using at least one of convolution, auto-correlation, or cross-correlation.

The one or more processors of the surgical system determine (812) a predicted time at which the physiological condition of the patient will meet a threshold physiological condition associated with the adverse surgical event based on a rate of change of the one or more physiological parameters. For example, threshold physiological parameters are stored in the threshold database 106. In some embodiments, the trend module 112 determines a predicted time at which a physiological condition of the patient will meet a threshold physiological condition associated with an adverse surgical event based on a rate of change of one or more physiological parameters measured by the sensors 118*a-n*. The trend module 112 is illustrated and described in more detail with reference to FIG. 1.

Responsive to determining the predicted time, the one or more processors of the surgical system transmit (816) a first alert to one or more robotic surgical controls of the surgical system to adjust the surgery prior to the predicted time. The surgical procedure can be modified or terminated by the surgeon or the robotic controls to avoid the threshold physiological condition and the adverse surgical event. For example, the patient can be cooled down if she is overheating, heart rate can be reduced, or another intervention can be applied.

The one or more processors of the surgical system determine (820) that the physiological condition of the patient has met the threshold physiological condition. In some embodiments, the alert condition module 110 or the base alert module 108 determines that a physiological condition of the patient has met a threshold physiological condition (e.g., hypothermia, elevated blood pressure, minimal pulse, etc.) based on the sensor data. Hypothermia is a potential adverse event connected to anesthesia. During surgery, the patient is exposed to a cold environment and has fluids that are typically colder than the patient's core body temperature being infused. The standard process of thermoregulation would typically be enough to overcome this, but that response can be compromised under anesthesia. Thus, temperature monitoring and perioperative thermoregulation methods are a critical part of the surgery.

Responsive to determining that the physiological condition of the patient has met the threshold physiological condition, the one or more processors of the surgical system transmit (824) a second alert to the one or more robotic surgical controls to terminate the surgery. In some embodiments, responsive to determining that the physiological condition of the patient has met a threshold physiological condition, the alert condition module 110 or the base alert module 108 transmits an alert to one or more robotic surgical controls to terminate the surgery. This alert is sometimes referred to as a second alert because it can be transmitted after transmitting a first alert predicting an adverse event.

Figure 9:
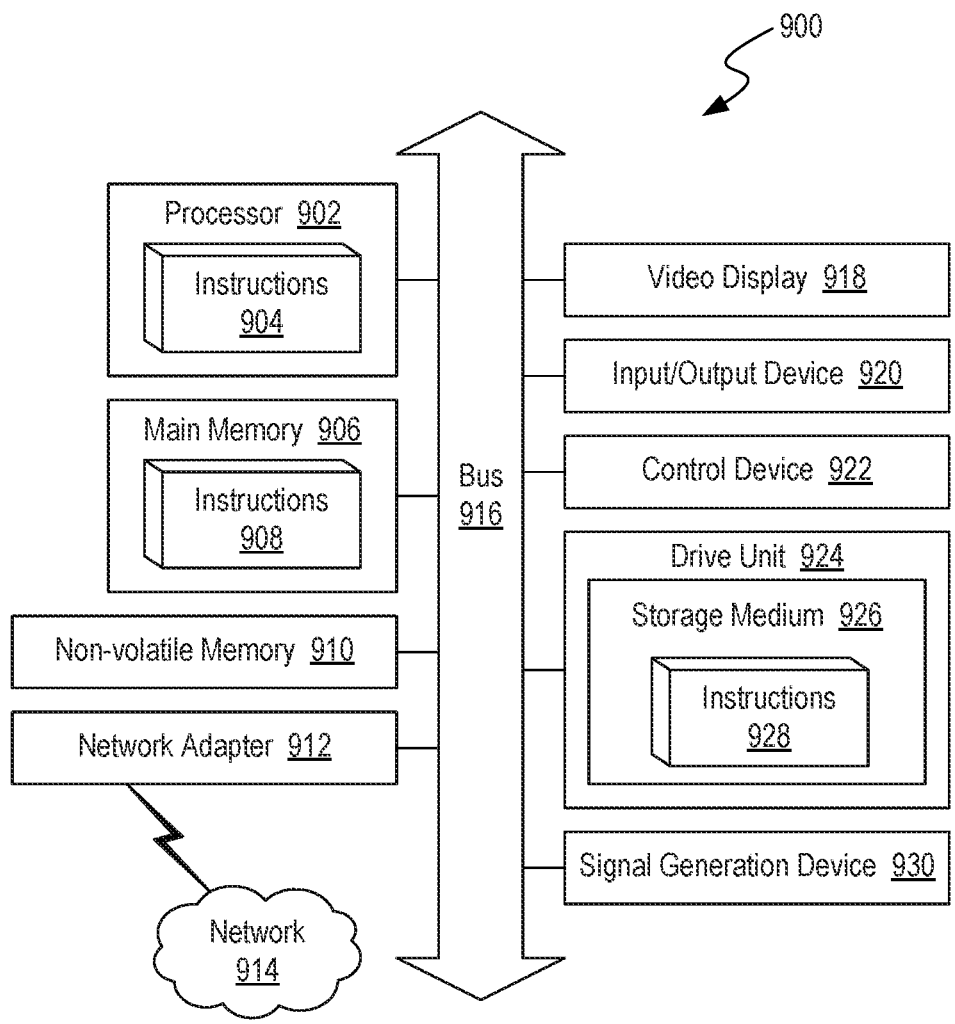
FIG. 9 is a block diagram illustrating an example computer system, in accordance with one or more embodiments.

FIG. 9 is a block diagram illustrating an example computer system 900, in accordance with one or more embodiments. Components of the example computer system 900 can be used to implement the patient monitoring network 102, the base alert module 108, the interface 120, and the sensors 118*a-n* illustrated and described in more detail with reference to FIG. 1. At least some operations described herein can be implemented on the computer system 900.

The computer system 900 can include one or more central processing units ("processors") 902, main memory 906, non-volatile memory 910, network adapter 912 (e.g., network interface), video display 918, input/output devices 920, control device 922 (e.g., keyboard and pointing devices), drive unit 924 including a storage medium 926, and a signal generation device 930 that are communicatively connected to a bus 916. The bus 916 is illustrated as an abstraction that represents one or more physical buses and/or point-to-point connections that are connected by appropriate bridges, adapters, or controllers. The bus 916, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 900 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality system (e.g., a head-mounted display), or another electronic device capable of executing a set of instructions (sequential or otherwise) that specify action(s) to be taken by the computer system 900.

While the main memory 906, non-volatile memory 910, and storage medium 926 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 928. The term "machine-readable medium" and "storage medium" shall also be taken to include any medium that is capable of storing, encoding, or carrying a set of instructions for execution by the computer system 900.

In general, the routines executed to implement the embodiments of the disclosure may be implemented as part of an operating system or a specific application, component, program, object, module, or sequence of instructions (collectively referred to as "computer programs"). The computer programs typically include one or more instructions (e.g., instructions 904, 908, 928) set at various times in various memory and storage devices in a computing device. When read and executed by the one or more processors 902, the instruction(s) cause the computer system 900 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 910, floppy and other removable disks, hard disk drives, optical discs (e.g., Compact Disc Read-Only Memory (CD-ROMs), Digital Versatile Discs (DVDs)), and transmission-type media such as digital and analog communication links.

The network adapter 912 enables the computer system 900 to mediate data in a network 914 with an entity that is external to the computer system 900 through any communication protocol supported by the computer system 900 and the external entity. The network adapter 912 can include a network adapter card, a wireless network interface card, a router, an access point, a wireless router, a switch, a multi-layer switch, a protocol converter, a gateway, a bridge, a bridge router, a hub, a digital media receiver, and/or a repeater.

The network adapter 912 may include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications may be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms may on occasion be used interchangeably.

Consequently, alternative language and synonyms may be used for any one or more of the terms discussed herein, and no special significance is to be placed upon whether or not a term is elaborated or discussed herein. Synonyms for certain terms are provided. A recital of one or more synonyms does not exclude the use of other synonyms. The use of examples anywhere in this specification, including examples of any term discussed herein, is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications may be implemented by those skilled in the art.

We claim:

1. A method comprising:
   training, by a surgical system, a machine learning module to predict adverse surgical events for patients undergoing surgery based on stored surgical data associated with the one or more adverse surgical events;
   monitoring, by one or more monitoring devices of the surgical system, one or more physiological parameters of a patient undergoing surgery, the one or more physiological parameters describing a physiological condition of the patient;

extracting, by one or more processors of the surgical system, a feature vector from the one or more physiological parameters using the machine learning module, the feature vector indicative of one or more vital signs of the patient;

intra-operatively avoiding an adverse surgical event by:
determining, by the one or more processors, a predicted time during the surgery at which the physiological condition of the patient will meet a threshold physiological condition associated with the adverse surgical event using the machine learning module based on the feature vector; and responsive to determining the predicted time, transmitting, by the surgical system, a first alert to one or more robotic surgical controls of the surgical system to adjust the surgery prior to the predicted time;

determining, by the one or more processors, that the physiological condition of the patient has met the threshold physiological condition; and responsive to determining that the physiological condition of the patient has met the threshold physiological condition, transmitting, by the one or more processors, a second alert to the one or more robotic surgical controls to terminate the surgery.

2. The method of claim 1, further comprising correlating the one or more physiological parameters to the stored surgical data, wherein the correlating comprises:
comparing, by the surgical system, patterns in the stored surgical data to the one or more physiological parameters using at least one of convolution, auto-correlation, or cross-correlation.

3. The method of claim 1, further comprising correlating the one or more physiological parameters to the stored surgical data, wherein the correlating comprises:
comparing, by the surgical system, the one or more physiological parameters to stored electronic health records using regression analysis, wherein the stored surgical data comprises the stored electronic health records.

4. The method of claim 1, wherein the one or more monitoring devices comprise at least one of a heart-rate monitor, pulse oximeter, capnography monitor, blood pressure monitor, body temperature monitor, or electrocardiogram machine.

5. The method of claim 1,
wherein the robotic surgical controls comprise a surgical tower for minimally invasive surgery,
wherein the threshold physiological condition is based on one or more identified patterns of the one or more physiological parameters, and
wherein the first alert includes one or more actions to respond to the physiological condition.

6. The method of claim 1, further comprising correlating the one or more physiological parameters to the stored surgical data, wherein the correlating comprises:
identifying, by the surgical system, the one or more adverse surgical events using an electronic health record of the patient.

7. The method of claim 1, further comprising:
transmitting, by the surgical system, a third alert to the one or more robotic surgical controls responsive to a plurality of the one or more physiological parameters being proximate to threshold physiological parameters.

8. A system comprising:
one or more computer processors; and
a non-transitory computer-readable storage medium storing computer instructions, which, when executed by the one or more computer processors, cause the one or more computer processors to:
monitor, by one or more monitoring devices of a surgical system, one or more physiological parameters of a patient undergoing surgery, the one or more physiological parameters describing a physiological condition of the patient;

extract a feature vector from the one or more physiological parameters using a machine learning module, the feature vector indicative of one or more vital signs of the patient;

intra-operatively avoid an adverse surgical event by:
determining a predicted time during the surgery at which the physiological condition of the patient will meet a threshold physiological condition associated with the adverse surgical event using the machine learning module based on the feature vector, the machine learning module trained to predict adverse surgical events for patients undergoing surgery based on stored surgical data associated with the adverse surgical events; and responsive to determining the predicted time, transmitting a first alert to one or more robotic surgical controls of the surgical system to adjust the surgery prior to the predicted time;

determine that the physiological condition of the patient has met the threshold physiological condition; and responsive to determining that the physiological condition of the patient has met the threshold physiological condition, transmit a second alert to the one or more robotic surgical controls to terminate the surgery.

9. The system of claim 8, wherein the computer instructions, which when executed by the one or more computer processors, further cause the one or more computer processors to:
extract features from the one or more physiological parameters using the machine learning module for training the machine learning module, the features indicative of the one or more adverse surgical events.

10. The system of claim 8, wherein the computer instructions, which when executed by the one or more computer processors, further cause the one or more computer processors to correlate the one or more physiological parameters to the stored surgical data, wherein the correlating comprises:
identifying the adverse surgical events using the machine learning module based on the feature vector, the machine learning module trained based on the stored surgical data.

11. The system of claim 8, wherein the computer instructions, which when executed by the one or more computer processors, further cause the one or more computer processors to:
train the machine learning module, based on the stored surgical data, to correlate the physiological condition of the patient to the one or more adverse surgical events.

12. The system of claim 8, wherein the one or more monitoring devices comprise at least one of a heart-rate monitor, pulse oximeter, capnography monitor, blood pressure monitor, body temperature monitor, or electrocardiogram machine.

13. The system of claim 8,
wherein the robotic surgical controls comprise a surgical tower for minimally invasive surgery,
wherein the threshold physiological condition is based on one or more identified patterns of the one or more physiological parameters, and
wherein the first alert includes one or more actions to respond to the physiological condition.

14. The system of claim 8, wherein the computer instructions, which when executed by the one or more computer processors, further cause the one or more computer processors to correlate the one or more physiological parameters to the stored surgical data, wherein the correlating comprises:
identifying, by the computer system, the one or more adverse surgical events using an electronic health record of the patient.

15. A non-transitory computer-readable storage medium storing computer instructions, which, when executed by one or more computer processors, cause the one or more computer processors to:
monitor, by one or more monitoring devices of a surgical system, one or more physiological parameters of a patient undergoing surgery, the one or more physiological parameters describing a physiological condition of the patient;
extract a feature vector from the one or more physiological parameters using a machine learning module, the feature vector indicative of one or more vital signs of the patient;
intra-operatively avoid an adverse surgical event by:
determining a predicted time during the surgery at which the physiological condition of the patient will meet a threshold physiological condition associated with the adverse surgical event using the machine learning module based on the feature vector, the machine learning module trained to predict adverse surgical events for patients undergoing surgery based on stored surgical data associated with the adverse surgical events; and
responsive to determining the predicted time, transmitting a first alert to one or more robotic surgical controls of the surgical system to adjust the surgery prior to the predicted time;
determine that the physiological condition of the patient has met the threshold physiological condition; and
responsive to determining that the physiological condition of the patient has met the threshold physiological condition, transmit a second alert to the one or more robotic surgical controls to terminate the surgery.

16. The non-transitory computer-readable storage medium of claim 15, wherein the computer instructions, which when executed by the one or more computer processors, further cause the one or more computer processors to:
extract features from the one or more physiological parameters using the machine learning module for training the machine learning module, the features indicative of the one or more adverse surgical events.

17. The non-transitory computer-readable storage medium of claim 15, wherein the computer instructions, which when executed by the one or more computer processors, further cause the one or more computer processors to correlate the one or more physiological parameters to the stored surgical data, wherein the correlating comprises:
identifying the one or more adverse surgical events using the machine learning module based on the feature vector, the machine learning module trained based on the stored surgical data.

18. The non-transitory computer-readable storage medium of claim 15, wherein the computer instructions, which when executed by the one or more computer processors, further cause the one or more computer processors to:
train the machine learning module based on the stored surgical data, to correlate the physiological condition of the patient to the adverse surgical events.

19. The non-transitory computer-readable storage medium of claim 15, wherein the one or more monitoring devices comprise at least one of a heart-rate monitor, pulse oximeter, capnography monitor, blood pressure monitor, body temperature monitor, or electrocardiogram machine.

20. The non-transitory computer-readable storage medium of claim 15,
wherein the robotic surgical controls comprise a surgical tower for minimally invasive surgery,
wherein the threshold physiological condition is based on one or more identified patterns of the one or more physiological parameters, and
wherein the first alert includes one or more actions to respond to the physiological condition.

* * * * *